(12) United States Patent
Miller

(10) Patent No.: US 9,101,462 B2
(45) Date of Patent: Aug. 11, 2015

(54) SOFT TISSUE REPAIR APPARATUS AND METHOD

(75) Inventor: Drew Miller, Atlanta, GA (US)

(73) Assignee: FRANTZ MEDICAL DEVELOPMENT, LTD., Mentor, OH (US)

( * ) Notice: Subject to any disclaimer, the term of this patent is extended or adjusted under 35 U.S.C. 154(b) by 666 days.

(21) Appl. No.: 13/355,731

(22) Filed: Jan. 23, 2012

(65) Prior Publication Data

US 2012/0150296 A1 Jun. 14, 2012

Related U.S. Application Data

(62) Division of application No. 11/057,876, filed on Feb. 14, 2005, now abandoned.

(60) Provisional application No. 60/544,787, filed on Feb. 13, 2004.

(51) Int. Cl.
*A61F 2/08* (2006.01)
*A61B 17/00* (2006.01)
*A61B 17/04* (2006.01)

(52) U.S. Cl.
CPC ..... *A61F 2/0811* (2013.01); *A61B 2017/00557* (2013.01); *A61B 2017/0414* (2013.01); *A61B 2017/0427* (2013.01); *A61B 2017/0429* (2013.01); *A61B 2017/0459* (2013.01); *A61B 2017/0461* (2013.01); *A61B 2017/0464* (2013.01); *A61F 2002/087* (2013.01); *A61F 2002/0829* (2013.01); *A61F 2002/0835* (2013.01); *A61F 2002/0882* (2013.01)

(58) Field of Classification Search
CPC ................ A61F 2002/0852; A61F 2002/0882
USPC .......... 623/13.11, 13.12, 13.13, 13.14, 13.15, 623/13.16
See application file for complete search history.

(56) References Cited

U.S. PATENT DOCUMENTS

| | | |
|---|---|---|
| 3,991,766 A | 11/1976 | Schmitt et al. |
| 4,534,349 A | 8/1985 | Barrows |
| 4,997,433 A | 3/1991 | Goble et al. |
| 5,061,283 A | 10/1991 | Silvestrini |

(Continued)

FOREIGN PATENT DOCUMENTS

| | | |
|---|---|---|
| RU | 2166917 | 9/1997 |
| WO | 96/16612 | 6/1996 |
| WO | 03/075800 | 9/2003 |

OTHER PUBLICATIONS

Sekiya et al., Arthroscopic Biceps Tenodesis Using the Percutaneous Intra-Articular Transtendon Technique, Dec. 2003, Arthroscopy: The Journal of Arthroscopic and Related Surgery, vol. 19 No. 10, pp. 1137-1141.*

(Continued)

*Primary Examiner* — Thomas J Sweet
*Assistant Examiner* — Wade P Schutte
(74) *Attorney, Agent, or Firm* — Tarolli, Sundheim, Covell & Tummino LLP

(57) ABSTRACT

The present invention relates to a method for treating a first biological soft tissue. A biological soft tissue implant is attached to a first damaged biological soft tissue such that the biological soft tissue implant is capable of interacting with a second biological soft tissue or bone to prevent the first biological soft tissue from retracting beyond a predetermined position.

21 Claims, 39 Drawing Sheets

(56) References Cited

U.S. PATENT DOCUMENTS

| | | | |
|---|---|---|---|
| 5,250,058 A | 10/1993 | Miller et al. | |
| 5,425,767 A * | 6/1995 | Steininger et al. | 623/13.14 |
| 5,609,636 A | 3/1997 | Kohrs et al. | |
| 5,713,912 A | 2/1998 | Porter | |
| 5,723,008 A | 3/1998 | Gordon | |
| 5,800,544 A * | 9/1998 | Demopulos et al. | 623/13.13 |
| 5,916,224 A | 6/1999 | Esplin | |
| 5,984,966 A | 11/1999 | Keima et al. | |
| 5,984,967 A | 11/1999 | Zdeblick et al. | |
| 6,024,758 A | 2/2000 | Thal | |
| 6,074,409 A | 6/2000 | Goldfarb | |
| 6,102,947 A | 8/2000 | Gordon | |
| 6,102,948 A | 8/2000 | Brosnahan, III | |
| 6,106,556 A | 8/2000 | Demopulos et al. | |
| 6,322,571 B1 | 11/2001 | Adams | |
| 6,342,060 B1 | 1/2002 | Adams | |
| 6,443,963 B1 | 9/2002 | Baldwin et al. | |
| 6,632,245 B2 | 10/2003 | Kim | |
| 6,712,830 B2 | 3/2004 | Esplin | |
| 7,001,411 B1 | 2/2006 | Dean | |
| 7,414,168 B2 | 8/2008 | Lebner | |
| 2001/0014825 A1 | 8/2001 | Burke et al. | |
| 2001/0051815 A1 | 12/2001 | Esplin | |
| 2002/0072806 A1 | 6/2002 | Buskirk et al. | |
| 2003/0114865 A1 | 6/2003 | Sater | |
| 2003/0130694 A1 | 7/2003 | Bojarski et al. | |
| 2003/0130735 A1 | 7/2003 | Rogalski | |
| 2004/0153103 A1 | 8/2004 | Schwartz et al. | |
| 2004/0193217 A1 | 9/2004 | Lubbers et al. | |
| 2004/0244609 A1 | 12/2004 | Muhs | |
| 2005/0197699 A1 * | 9/2005 | Jacobs et al. | 623/13.14 |

OTHER PUBLICATIONS

Tibone et al., Shoulder Arthroscopy, 2003, Springer Verlag, ISBN 978-1-4419-2972-3, pp. 71-80.*

* cited by examiner

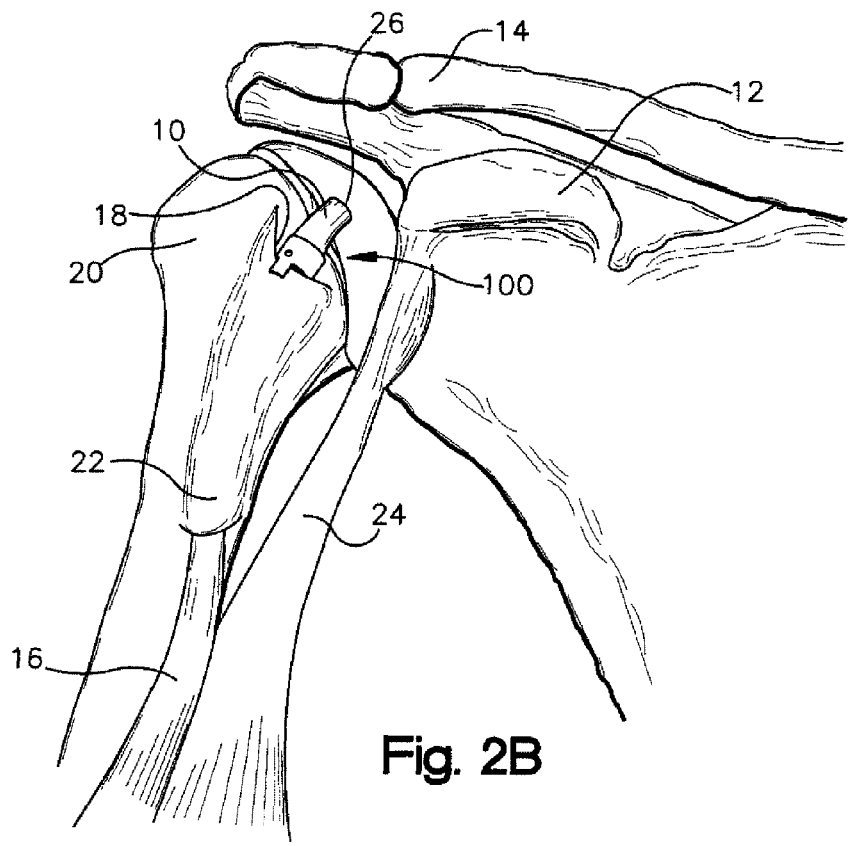
Fig. 2B
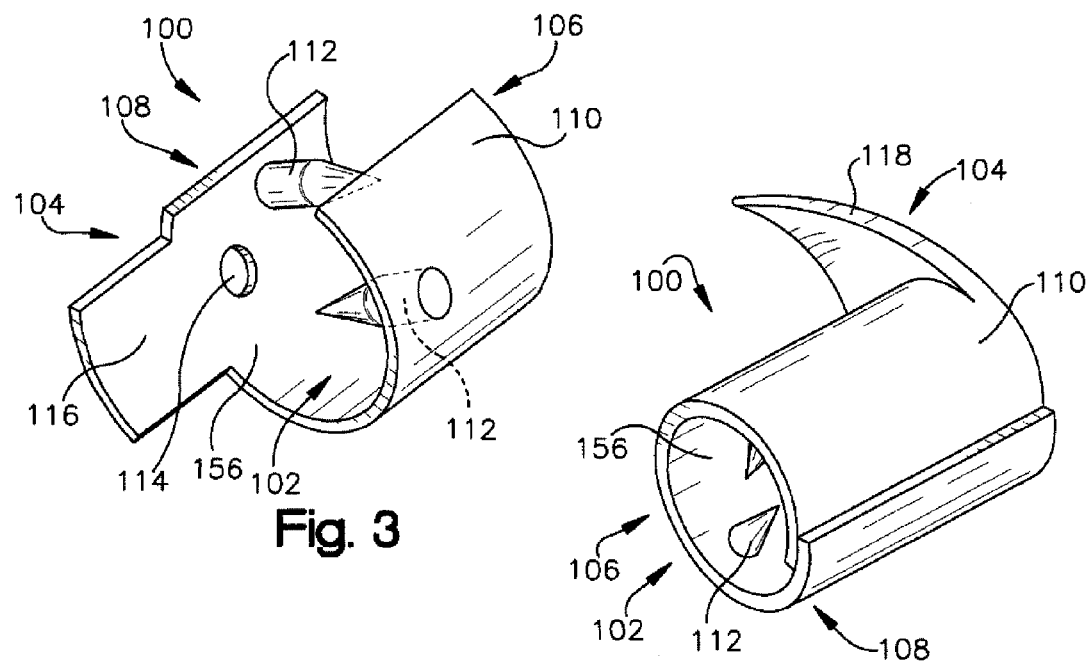
Fig. 3
Fig. 4

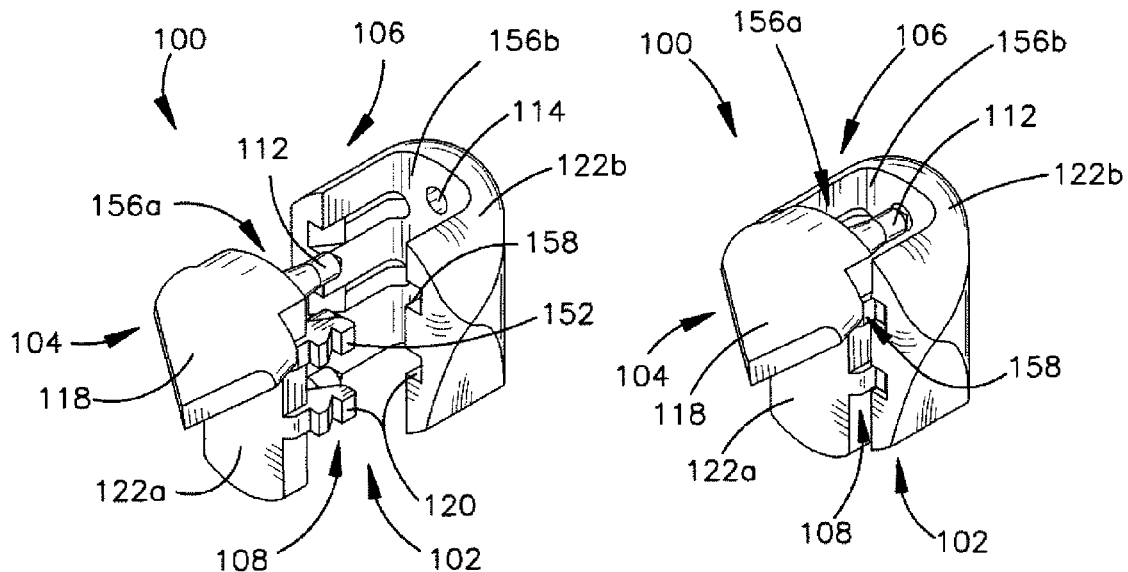
FIG. 5A
FIG. 5B
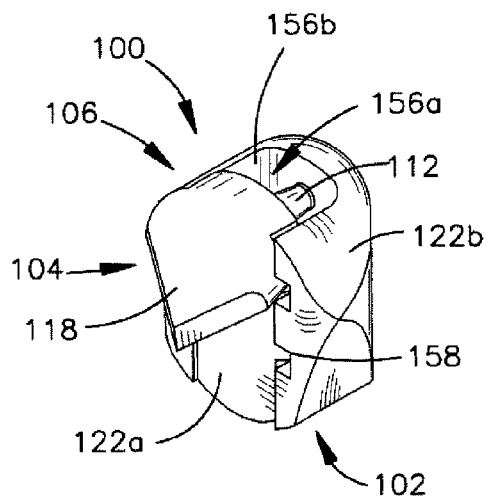
FIG. 5C
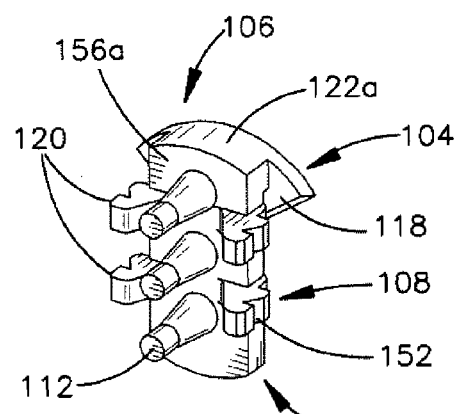
FIG. 5D
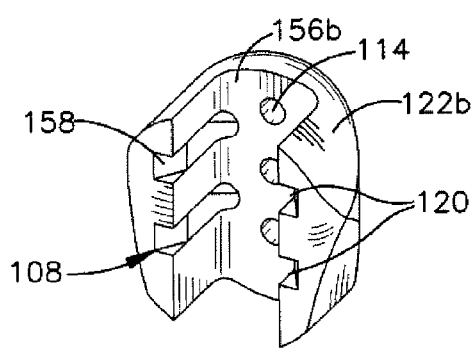
FIG. 5E

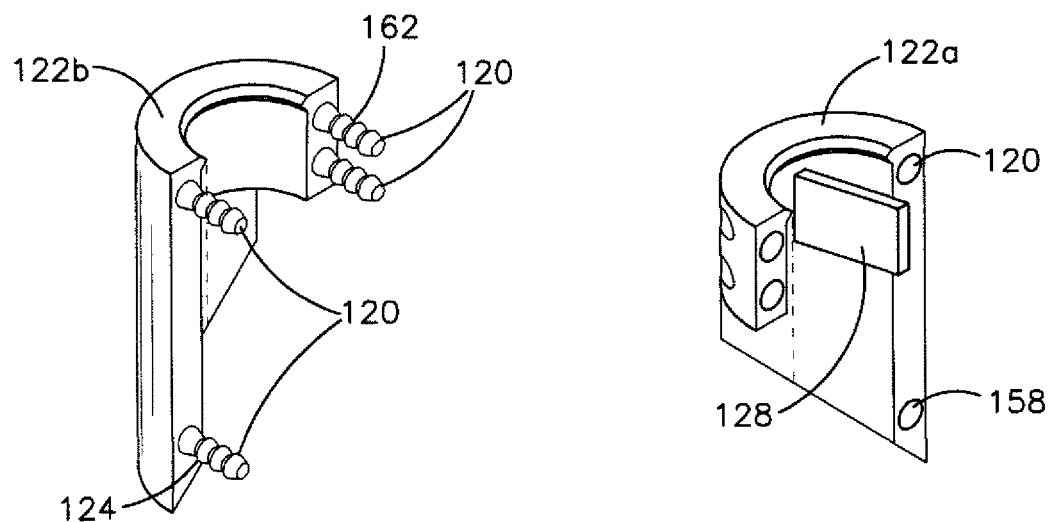
FIG. 13E
FIG. 13F
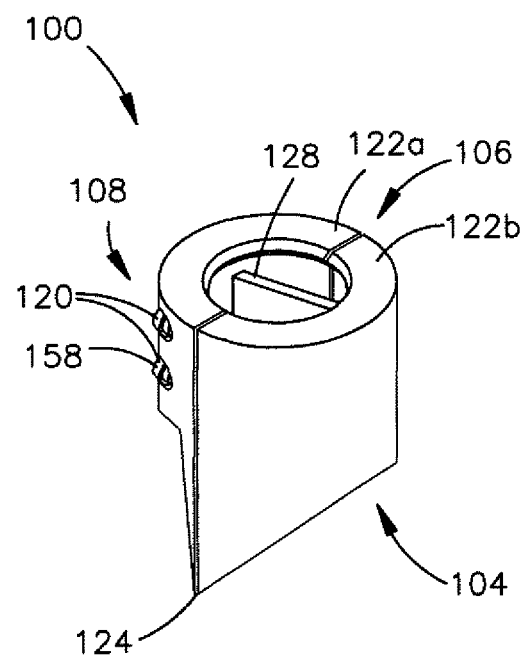
FIG. 13G

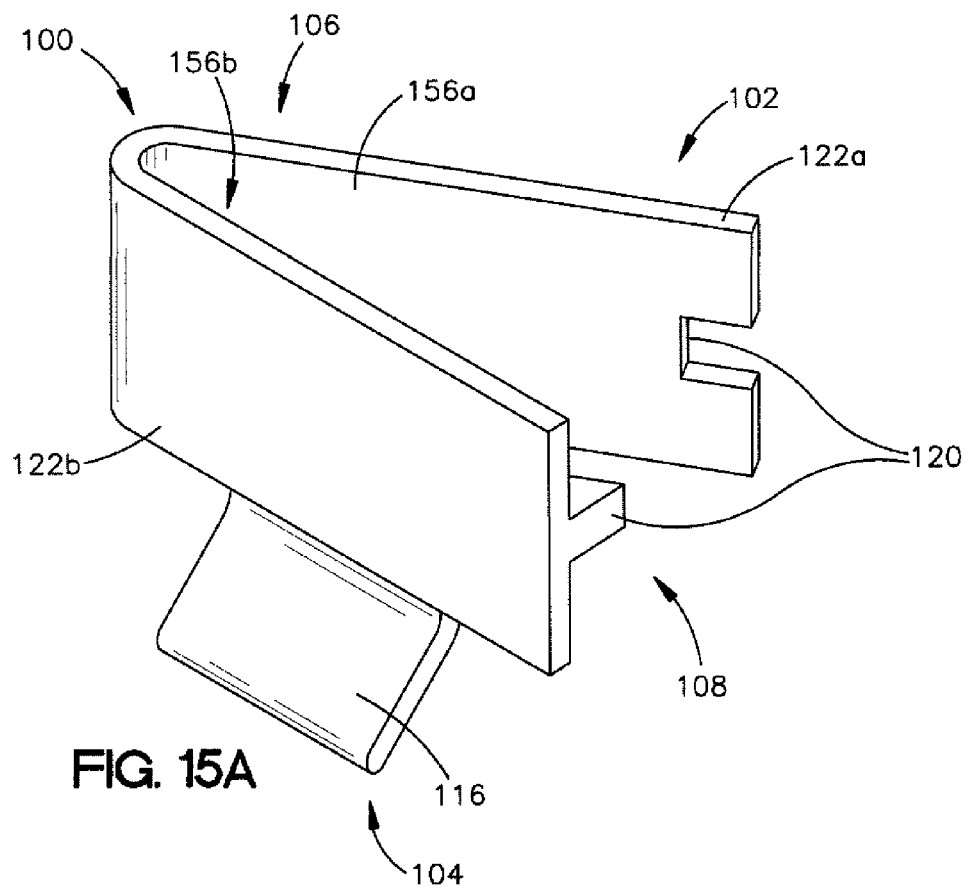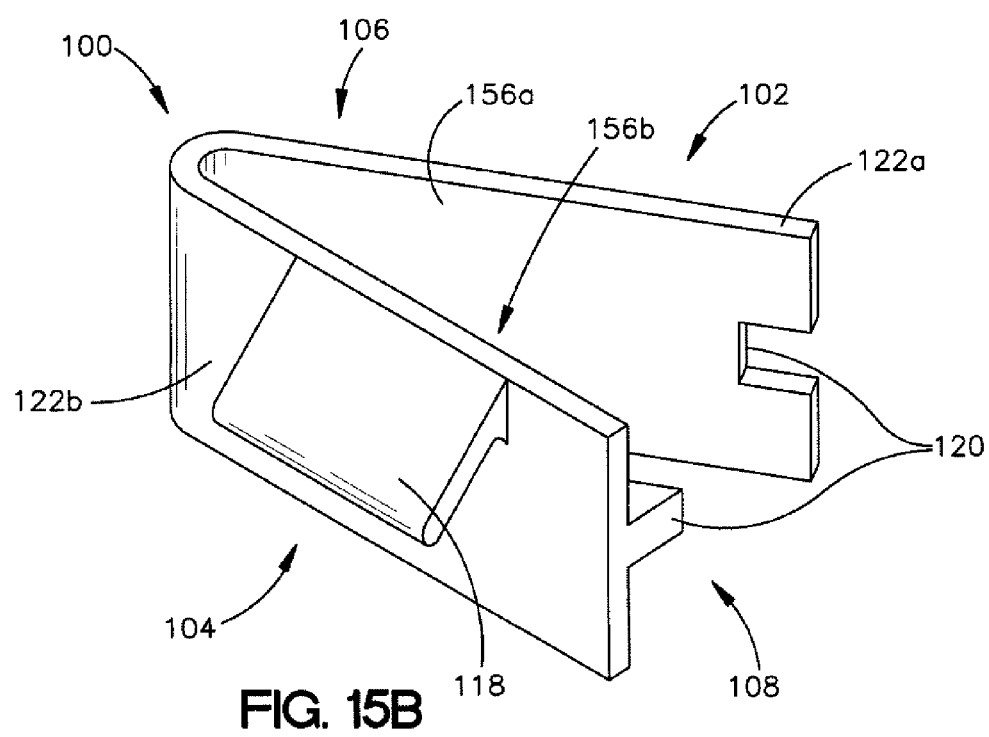

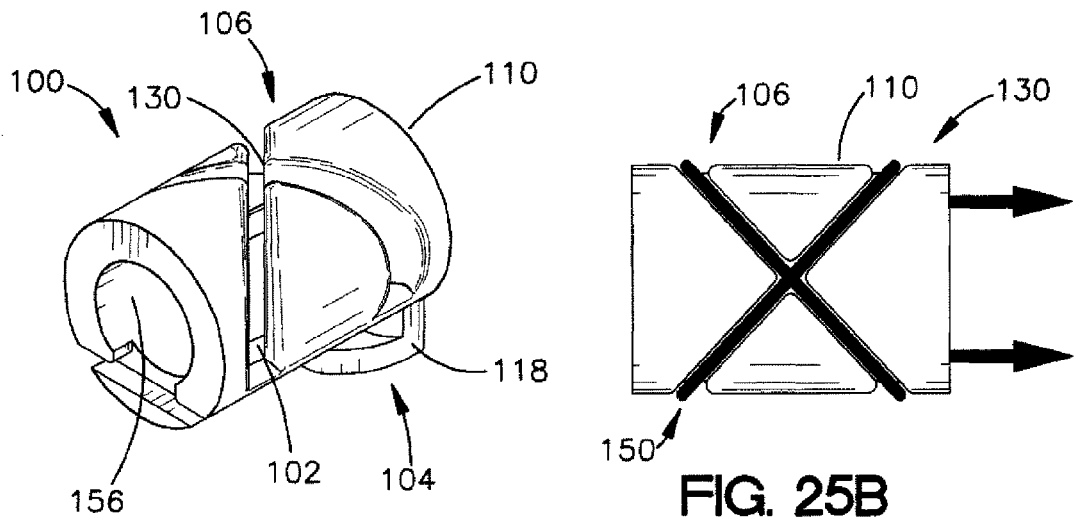
FIG. 25A
FIG. 25B
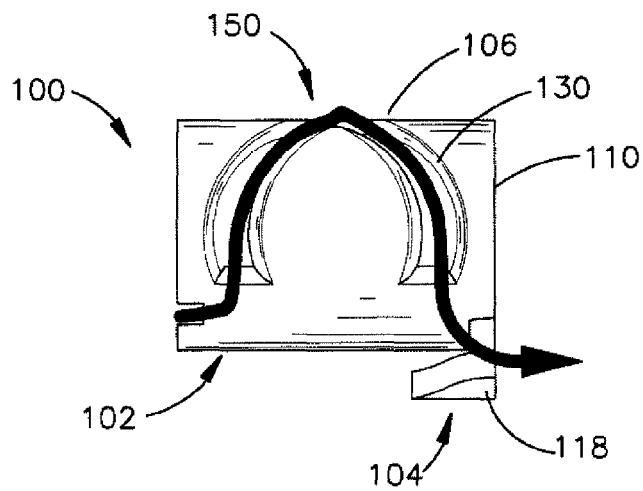
FIG. 25C
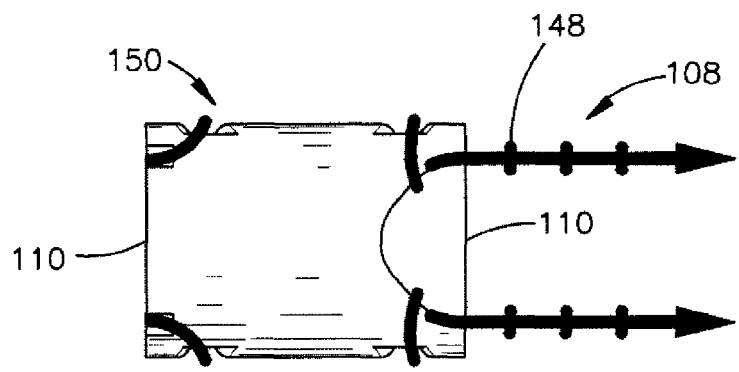
FIG. 25D

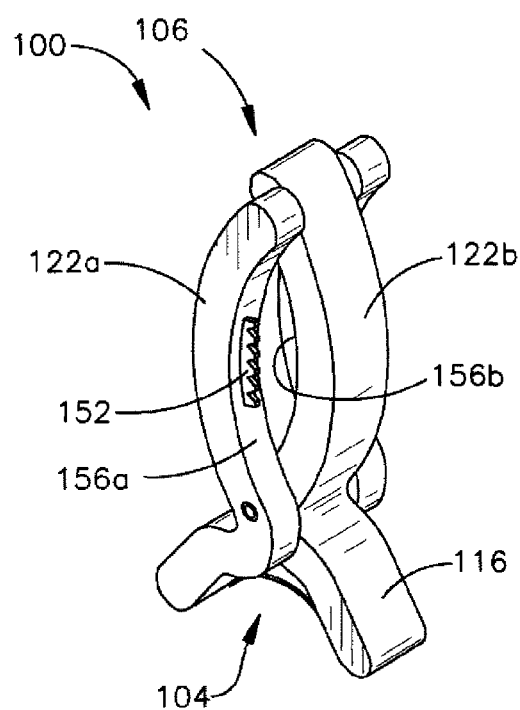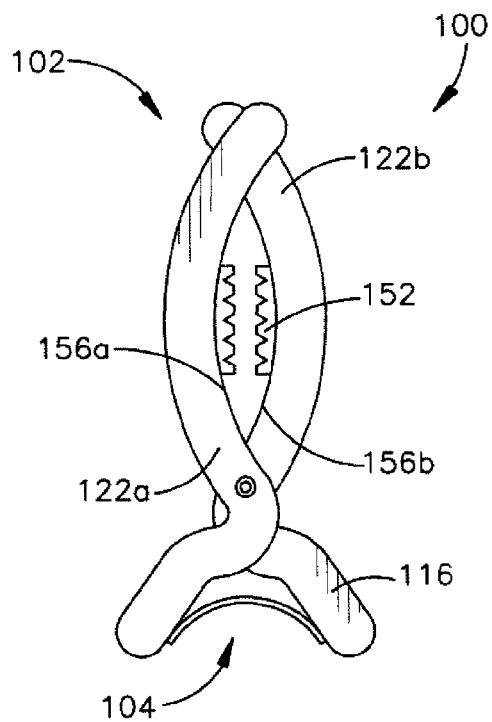
FIG. 29A    FIG. 29B
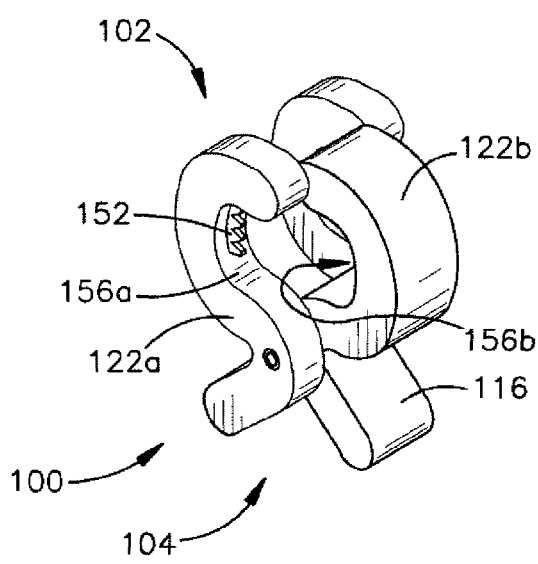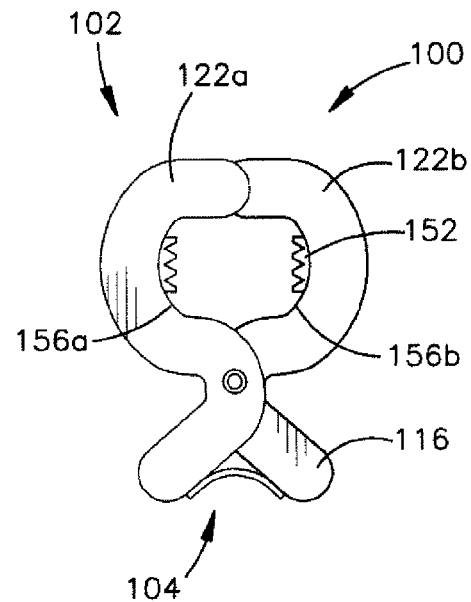
FIG. 30A    FIG. 30B

SOFT TISSUE REPAIR APPARATUS AND METHOD

RELATED APPLICATIONS

This application is a divisional of U.S. patent application Ser. No. 11/057,876, filed Feb. 14, 2005 now abandoned, which claims benefit of U.S. Provisional Patent Application Ser. No. 60/544,787, filed Feb. 13, 2004, the subject matter both of which are incorporated herein by reference.

FIELD OF THE INVENTION

The present invention relates generally to prostheses and methods for treating damaged biological soft tissue, and more specifically to a system and method for preventing biological soft tissue from retracting when severed and/or resected.

BACKGROUND OF THE INVENTION

The present invention may be applicable to the treatment of biological soft tissue either before or after the damaged biological soft tissue is severed and/or resected. This can be accomplished by the introduction of an implant device of the present invention. The present invention is described with reference to a damaged biceps tendon, but one of skill in the art will recognize that the present invention is not limited to the treatment of biceps tendons, and will also recognize the applicability of the present invention to other biological soft tissues.

Referring initially to FIG. 1A, a frontal view of the normal right human shoulder is illustrated. The biceps tendon 10 is a tendon that joins part of the biceps brachii, (i.e., the biceps muscle) to the shoulder. Specifically, the biceps tendon 10 inserts on the most superior portion of the glenoid labrum of the scapula 12 in the shoulder and extends downwardly to the biceps muscle 16 in the upper arm. The biceps tendon 10 is often referred to as the "long head" of the biceps brachii, ie: the long head of the biceps tendon. As can be further seen in FIG. 1A, the short head 24 of the biceps brachii also functions to attach the biceps muscle 16 to the shoulder. The biceps tendon 10 lies along the bicipital groove 18 in the humerus 20 and passes through a bicipital sheath 22. It is believed that the biceps tendon 10 contributes to stability of the shoulder, particularly when a patient's arm is disposed in certain orientations.

As a patient ages, the biceps tendon may become painful, inflamed, or may degenerate and fray beneath its upper attachment point, the point of attachment at the glenoid cavity. The degeneration and fraying of the biceps tendon is often due to abrasion against adjacent shoulder structures. This can result in tearing and cause the patient significant pain. One method of treating the pain caused by a partially torn biceps tendon 10 is to perform a procedure called a tenotomy. One benefit of a tenotomy is that it can easily be performed arthroscopically. As shown in FIG. 1B, a tenotomy involves severing the biceps tendon 10 at its upper end 26, so that it is detached from the glenoid. This procedure is typically effective at relieving the patient's pain symptoms caused by a degenerative and/or frayed biceps tendon. Despite severing the biceps tendon as part of a tenotomy, it has been found that the remaining structure supporting the biceps muscle 16, including the short head 24, provides adequate anterior stability for the shoulder, especially because the typical tenotomy patient is usually older and less physically active by the time the procedure is required. Since stability can be maintained despite a severed biceps tendon, a frayed and/or degenerative biceps tendon can be severed to alleviate associated pain.

Following a tenotomy procedure, patients often experience undesirable side effects. One of the most common side of these effects is known informally as a "Popeye Sign." As shown in FIG. 1C, a Popeye Sign develops when the biceps tendon 10 retracts down through the bicipital sheath 22. The retraction of the biceps tendon 10 causes the biceps 16 to sag and bulge in an unsightly way, as shown. The patient must therefore live with the resultant unsightly appearance and may also suffer from muscle cramping or aching. Consequently, this potential side effect is a significant deterrent to undergoing a tenotomy procedure and realizing the benefits of substantial pain relief.

Other approaches have been developed to try to obtain the benefits of pain relief while avoiding the side effect of a "Popeye Sign." One such approach, known as "biceps tenodesis," can be performed either by means of open or arthroscopic surgery. When performing a biceps tenodesis, the biceps tendon 10 is severed just as when performing a tenotomy. Unlike the tenotomy, however, in a biceps tenodesis, the biceps tendon 10 is sutured to the humerus 20 within the bicipital groove 18, using suture anchors to prevent the tendon from slipping downwardly through the sheath 22. Such a procedure is described in an article entitled *Arthroscopic Biceps Tenodesis Using the Percutaneous Intra-articular Transtendon Technique*, by Sekiya et al. published in the December 2003 edition *Arthroscopy: The Journal of Arthroscopic and Related Surgery*, Vol. 19, No. 10 (pp. 1137-1141). While a biceps tenodesis procedure is often successful, if performed using open surgical techniques, as is the present state of the art, it results in an unsightly scar and an extended recovery period when compared to a tenotomy. The arthroscopic procedure described in the identified article avoids the scarring issue, but is complex and difficult for most surgeons to perform using today's instrumentation. Moreover, the arthroscopic procedure still generally requires a longer recovery period than a simple tenotomy.

Thus, it is desirable for surgeons to be able to perform a procedure similar to a simple tenotomy and receive results comparable to those achieved by tenodesis.

SUMMARY OF THE INVENTION

According to an aspect of the invention, there is provided a biological soft tissue implant device comprising a fastener attachable to a first biological soft tissue; and an anchor capable of interacting with a second biological soft tissue or a bony tissue such that retraction of the first biological soft tissue is limited in at least one direction.

According to another aspect of the invention, there is provided a biological soft tissue implant device comprising a fastener attachable to a first biological soft tissue; and an anchor capable of interacting with a second biological soft tissue or a bony tissue such that when tension on the first biological soft tissue is relieved on one side of the biological soft tissue implant device, the interaction of the anchor and second biological soft tissue or bone creates tension on the first biological soft tissue on the opposite side of the biological soft tissue implant.

According to another aspect of the invention, there is a method for treating a biological soft tissue comprising attaching a biological soft tissue implant to the damaged biological soft tissue such that the biological soft tissue implant is capable of interacting with a second biological soft tissue or a bony tissue to prevent the damaged biological soft tissue from retracting beyond a predetermined position.

BRIEF DESCRIPTION OF THE DRAWINGS

FIG. 2B is similar to FIG. 2A and shows the biological soft tissue implant of 2A anchoring and interacting with the bicipital sheath as the biceps tendon retracts;

FIG. 3 illustrates a perspective view of an embodiment of the biological soft tissue implant of FIGS. 2A-B;

FIG. 4 illustrates a perspective view of another embodiment of the biological soft tissue implant of FIGS. 2A-B;

FIGS. 5A-C illustrate an embodiment of a biological soft tissue implant having cooperating parts that are snapably engageable where the implant is in different locking positions;

FIGS. 5D-E are perspective views of the cooperating parts of FIGS. 5A-5C;

FIGS. 13A-G illustrate another embodiment of a toggle biological soft tissue implant;

FIGS. 15A-C illustrate perspective views of other embodiments of clip-type biological soft tissue implants;

FIG. 25A illustrates a perspective view of an embodiment of a soft tissue implant designed to have a suture wrapped around the implant;

FIGS. 25B-D illustrate top, side and bottom elevation views, respectively, of the implant of FIG. 25A in conjunction with a suture;

FIGS. 29A-B illustrate perspective and front elevation views of another embodiment of a biological soft tissue implant having multiple biasedly engageable parts; and FIGS. 30A-B illustrate perspective and front elevation views of another embodiment of a biological soft tissue implant having multiple biasedly engageable parts.

DESCRIPTION OF THE PREFERRED EMBODIMENTS

Figure 1A:
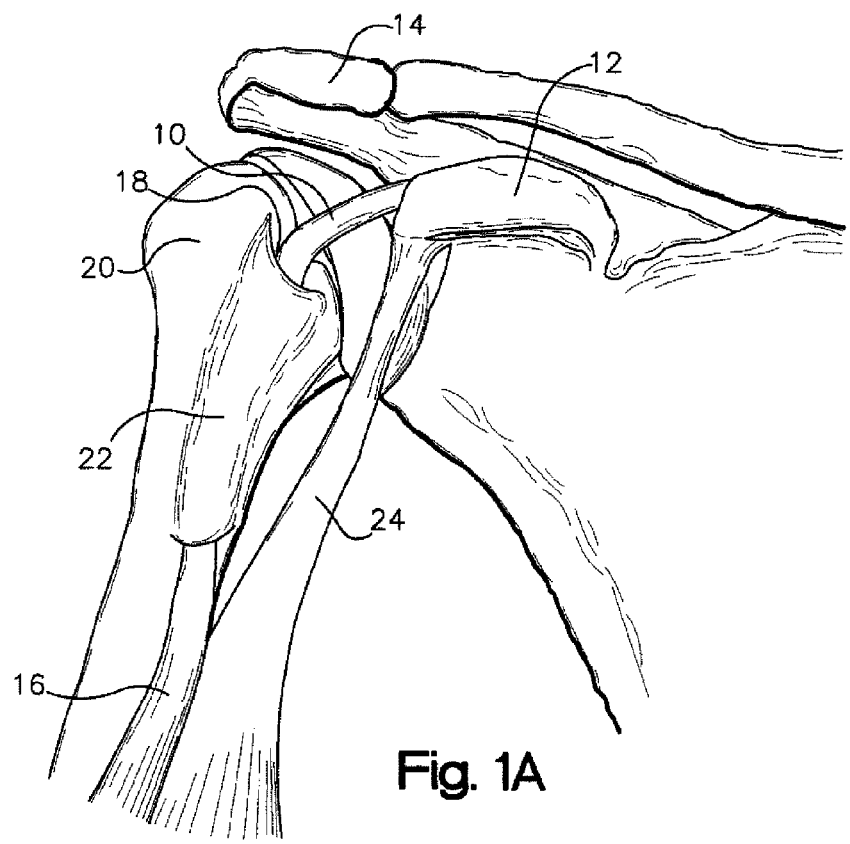
FIG. 1A is a view from the front of a typical normal right shoulder, showing the biceps tendon and related structure.
Figure 1B:
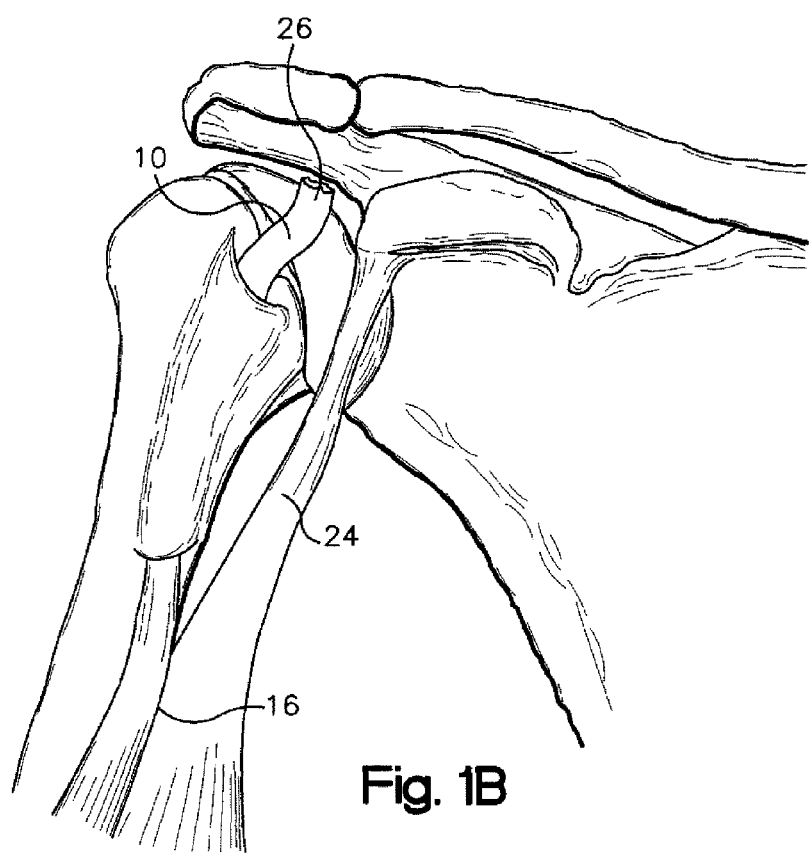
FIG. 1B is a view similar to FIG. 1A, wherein the biceps tendon has been cut in a tenotomy procedure in order to alleviate a patient's pain.
Figure 1C:
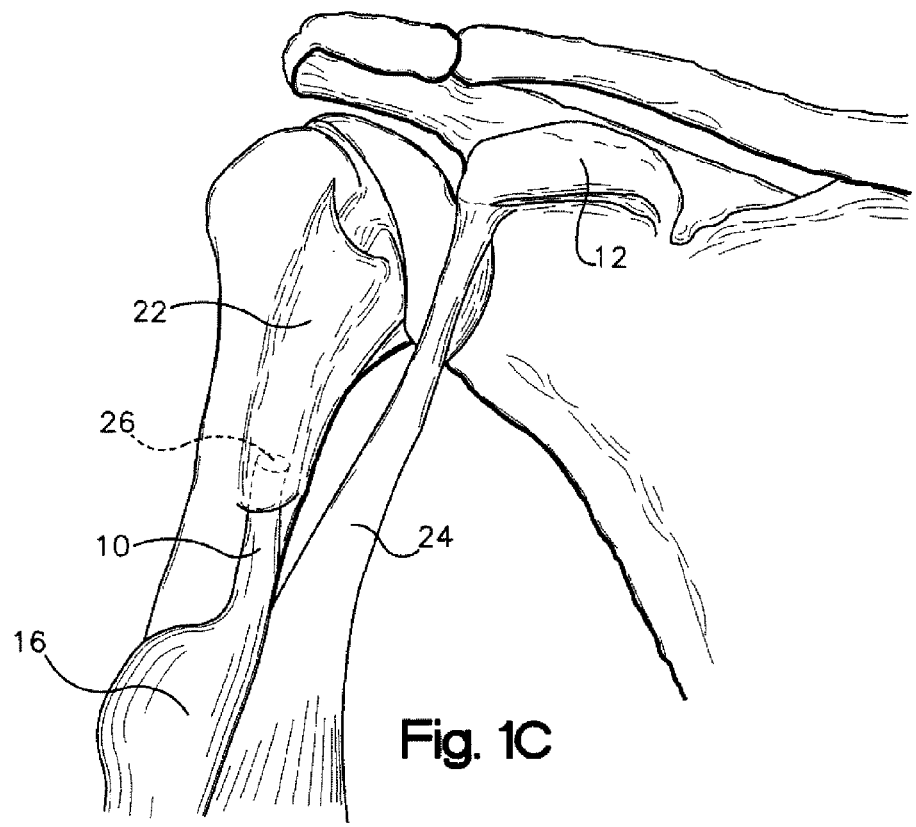
FIG. 1C is a view similar to FIGS. 1A-B, wherein the biceps tendon has slipped down through the bicipital sheath after the biceps tenotomy procedure, causing the biceps muscle to protrude or bulge in an unsightly manner known as a "Popeye Sign"
Figure 2A:
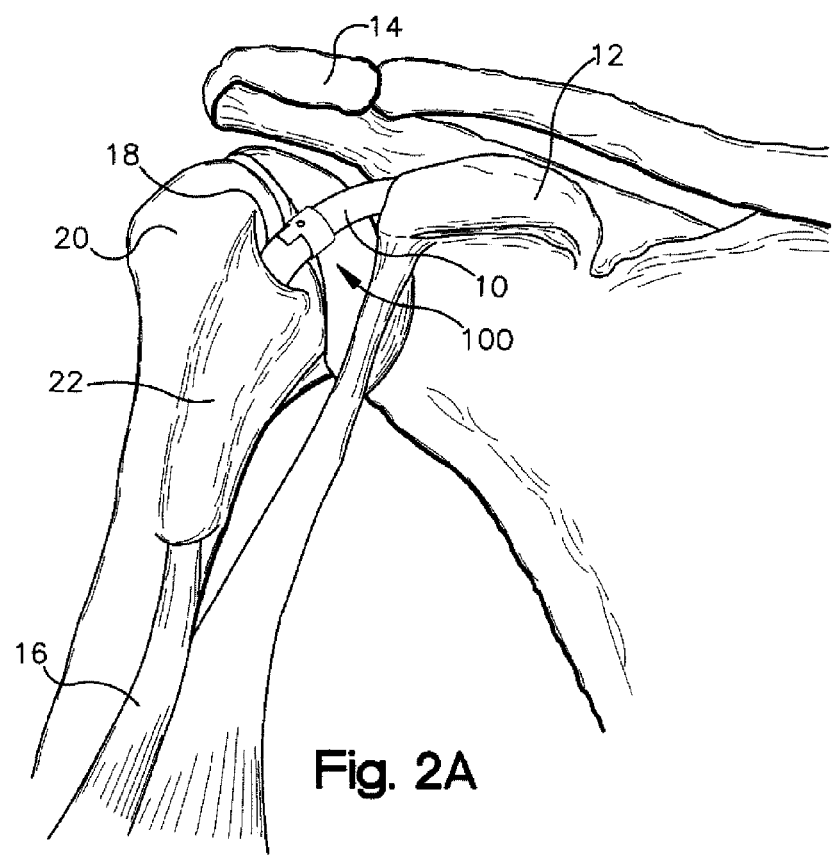
FIG. 2A is similar to FIGS. 1A-C and illustrates a biological soft tissue implant attached to the biceps tendon in accordance with the present invention.

Turning now to FIG. 2A, a biological soft tissue implant 100 is shown attached to a first biological soft tissue, the biceps tendon 10 in this example. FIG. 2B illustrates the implant 100 of FIG. 2A anchoring and interacting with a second biological soft tissue, in this case the bicipital groove 18 and bicipital sheath 22, as the biceps tendon 10 retracts into the bicipital sheath 22. Together, FIGS. 2A-B illustrate an inventive method for repairing a damaged biological soft tissue 10.

The implant 100 is configured such that once the biological soft tissue 10 is severed, as shown in FIG. 2B, the implant interacts with a second biological soft tissue or a bone to prevent the severed biologic soft tissue 10 from retracting beyond a predetermined position. In the example illustrated in FIGS. 2A-B, the tendon 10 is severed from the glenoid, such as during a tenotomy. Without the aid of the implant 100 of the present invention, the tendon 10 will likely retract down through the bicipital sheath 22. This causes what is known as the Popeye Sign condition, as is described above.

If the implant 100 is attached to the biceps tendon 10 prior to severing the tendon, however, the implant 100 will interact with the bony bicipital groove 18 and the tissue of the bicipital sheath 22, thereby capturing the biceps tendon 10 within the bicipital groove and causing tension on the tendon 10 between the implant 100 and the bicep 16. This prevents the tendon 10 from fully retracting beyond a predetermined position. This predetermined position may be any position that prevents an undesired effect associated with severing the biological soft tissue, such as a Popeye Sign. After capturing the tendon, the implant 100 places tension on one side of the biological soft tissue that is less than the tension placed on the biological soft tissue on the other side of the biological soft tissue implant 100. Moreover, any retraction of the first biological tissue further increases the interaction of the biological soft tissue implant 100 with the second biological soft tissue or the bony tissue. In other words, as the first biological tissue retracts, the implant 100 strengthens its connection or attachment with or to the second biological tissue.

It will be understood by those skilled in the art that the implant 100 may also be attached to the biological soft tissue after severing the biological soft tissue. In this case, the surgeon would sever the biological soft tissue while maintaining tension on the biological soft tissue before severing so that it does not retract upon being cut. In other words, a surgeon places tension on the damaged biological soft tissue prior to attaching the biological soft tissue implant. Before releasing the tension on the tissue, the surgeon would then attach the implant 100 to the tissue.

It should be noted that the bicipital sheath 22 boundaries include the transverse ligament and the bony bicipital groove 18. Therefore, the implant 100 may be configured so that it is of a greater size in one dimension than in another (i.e. it is in a shape other than round). Thus, when the implant 100 engages the bicipital groove 18, sheath 22 or transverse ligament, it may tend to self-align by action of the bicipital groove 18, and thus engage the boundaries of the sheath 22. Thus, fixation of the implant 100 may be achieved by engagement with the bicipital tunnel bounded by the bicipital sheath 22 and transverse ligament and the bony bicipital groove 18.

FIG. 3 illustrates the specific embodiment of the implant shown in FIGS. 2A-B having a fastener 102 and an anchor 104. The fastener 102 of the implant 100 is attached to the biceps tendon 10 as described above, either before of after severing the tendon 10. The retaining ring 110 of the fastener 102 is placed about the tendon 10 and squeezed or crimped to engage the tendon 10, the spikes 112 are forced to engage the tendon 10 and further secure the fastener 102 with the tendon 10. The crimping of the implant 100 can be accomplished by any crimping tools known in the art. Preferably, the crimping tools are configured so that the implant 100 can be crimped during an arthroscopic procedure without causing the procedure to become any more invasive due to crimping the implant 100. The spikes 112 may be forced into the tendon 10 or even penetrate through the tendon 10 to provide a secure connection or anchorage of the implant 100.

Once the fastener 102 is attached to the tendon 10, the implant 100 is allowed to move down until the anchor 104 of the implant 100 engages an outer surface of the sheath 22. This engagement occurs when the tab 116 of the anchor 104 is allowed to contact an outer surface of the sheath 22. Thus, the implant 100 attaches to the tendon 10 via the fastener 102 and then anchors to the sheath 22 via engagement of the tab 116 of the anchor 104 with the outer surface of the sheath 22. The securing of the fastener 102 can occur either before or after the severing of the biceps tendon 10 from the glenoid, as previously described. Likewise the engagement of the anchor 104 of the implant 100 with the sheath 22 can occur either before or after the severing of the biceps tendon 10.

Embodiments of the present inventions includes a variety of biological soft tissue implants designed to attach to damaged biological soft tissue, such as a tendon that has been torn or detached on one side. Each of the various implant embodiments includes a fastener for attaching the implant to a damaged biological soft tissue. The fasteners may include, for example, alone or in combination, spikes, ridges, grooves, at least one latch, at least one suture passing through the first biological soft tissue, at least one suture wrapped around the first biological soft tissue, at least one hinge, at least one crimping deformation, engageable opposing parts, at least one retaining ring, at least one gripping beam, at least one hook and capture mechanism, as well as other like fasteners. The mechanism by which the opposing parts engage may also vary. For example, the engageable opposing parts may be snapably engageable, slidably engageable, hookably engageable, rotatably engageable, or biasedly engageable.

The various types of fasteners may also include both an engaging element for engaging the implant with the damaged biological soft tissue and a locking element to maintain that engagement in place. The engaging element may include, alone or in combination, at least two cooperating parts for trapping the first biological soft tissue, a suture passable through the first biological soft tissue, a suture wrappable around the first biological soft tissue, a suture and component combination wherein the suture clinches the first biological soft tissue against the component, at least one hook and capture mechanism, at least one spike for piercing the first biological soft tissue, or at least one barb for piercing the first biological soft tissue, as well as other elements suitable for engaging biological soft tissue or bone.

The locking element may also vary. For example, the locking element may include, alone or in combination, snap-fitting parts, crimping, biasing, at least one knot, press-fitting, at least one thread, at least one barb, riveting, swaging, cold shaping, welding or the like.

In order to improve engagement with the damaged biological soft tissue, the implant may also include, alone or in combination, one or more gripping surfaces, which may have barbs, spikes, holes, slots, ridges, grooves, serrations, teeth, textured surfaces, or other gripping mechanisms.

Each of the various implant embodiments also includes an anchor that is capable of interacting with another biological soft tissue or bone in order to prevent the damaged biological soft tissue from retracting. The anchor of each of the various embodiments may be designed such that once tension is tension on the damaged biological soft tissue is relieved on one side of the biological soft tissue implant device (such as by severing the damaged biological soft tissue or by a surgeon releasing severed biological soft tissue) the interaction of the anchor and second biological soft tissue or bone creates tension on the opposite side of the biological soft tissue implant.

The specific mechanism by which the anchor interacts with another biological soft tissue or bone may vary. For example, the anchor may include, alone or in combination, at least one barb, at least one spike, at least one flap, at least one bar, at least one beam, at least one hook, a pointed implant end configured to anchor when the implant device toggles, at least one expansion mechanism, or other like structures suitable for anchoring the implant to biological soft tissue or to bone. Where the anchor is a pointed implant end configured to anchor when the implant device toggles, tension on the damaged biological soft tissue may cause the toggling of the implant device, thereby causing the interaction with a second biological soft tissue.

As will be understood by one of skill in the art, the implants may be fabricated of any known biocompatible material, including suitable metals, plastics, and/or resorbable materials. Plastics may be more suitable for some embodiments, while metal may be more suitable for others.

It will also be understood by one of skill in the art that the implants of the present invention may be configured for use during arthroscopic procedures. Arthroscopic procedures are often performed with the aid of a cannula. Thus, it may be preferable for the implants of the present invention to fit within the diameter of a cannula.

Turning to FIG. 3, one embodiment of the implant 100 of the present invention is illustrated. As illustrated in FIG. 3, the implant 100 includes a fastener 102 and anchor 104. The fastener 102 includes spikes 112 and a retaining ring 110, as well as a gripping surface 156 with a hole 114 extending through the gripping surface 156. The anchor 104 of the implant 100 of FIG. 3 is a tab 116. In practice, the implant 100 of FIG. 3 is either a flexible material such as a plastic or a crimpable material such as a metal appropriate for implant uses. The fastener 102 acts as a retaining ring 110 with a gripping surface 156 located on the interior surface of the retaining ring 110 for engaging the exterior surface of the tendon.

In operation, the retaining ring 110 of the fastener 102 is placed around the tendon 10. If the fastener 102 is fabricated of a flexible material, it will typically have a smaller inner diameter than the outer diameter of the tendon and can be opened via pressure or other conventional means in order to slip it around the tendon 10. Once the fastener 102 is slipped around the tendon 10, the pressure is removed and the retaining ring 110 closes securely around the outer diameter of the tendon. If the fastener 102 is fabricated from a metal, it can be crimped about the outer diameter of the tendon in order to secure it in place around the tendon. Again, the implant 100 may be crimped using any crimping tools known in the art. Preferably, the crimping tools are configured so that the implant 100 can be crimped during an arthroscopic procedure without causing the procedure to become any more invasive due to crimping the implant 100.

Turning now to FIG. 4, an alternate embodiment of the implant of FIG. 3 is illustrated. The implant 100 includes a fastener 102 and anchor 104. The fastener 102 includes spikes 112 and a retaining ring 110 and a hook 118 as an anchor 104. This implant 100 is deployed in a manner similar to that of FIG. 3 except that the hook 118 may rest against the top of the sheath 22 or may attach to an inner surface of the sheath 22. One of skill in the art will readily appreciate that spikes do not have to be included if the crimping force is significant enough to obtain a strong attachment between the gripping surface 156 and the tendon 10.

FIGS. 5A-E illustrate an embodiment of a biological soft tissue implant having cooperating parts 122a and 122b that are snapably engageable. FIGS. 5A-C illustrate is a biological soft tissue implant 100 having a fastener 102 and anchor 104. The anchor 104 includes a hook 118. The fastener 102 includes cooperating parts 122a and 122b, which are snapably engageable opposing parts having gripping surfaces 156a and 156b with holes 114 on gripping surfaces 156b. FIGS. 5D-E are perspective views of the cooperating parts 122a and 122b, respectively. The fastener 102 can be described as including both an engaging element 106 and a locking element 108. The engaging element 106 includes the cooperating parts 122a and 122b for trapping the biological soft tissue, the spikes 112 and the gripping surfaces 156a and 156b with holes 114. The locking element 108 includes snap-fitting parts 120, which include teeth 152 and receivers 158.

In operation the fastener 102 engages the biological soft tissue between the cooperating parts 122a and 122b. When the cooperating parts 122a and 122b are brought together with the soft tissue therebetween, the fastener 102 engages the biological soft tissue. Specifically, the spikes 112 of the fastener 102 puncture the tissue and engage the holes 114. Once engaged, the fastener 102 also includes a locking element 108. The locking element 108 in the specific embodiment shown includes multiple locking positions as shown in FIGS. 5B-C. Thus, the fastener 102 can snap into two separate locked positions. The locking element 108 of the fastener 102 includes teeth 152 and receivers 158 to allow the cooperating parts 122a and 122b to snap together. When the cooperating parts 122a and 122b are snapped together, the biological soft tissue is engaged and locked so that it is held securely between the cooperating parts 122a and 122b.

Once the fastener 102 is engaged and locked, tension on the biological soft tissue can be relieved such that the soft tissue begins to retract. The hook 118 of the anchor 104 is configured to engage a second biological soft tissue or bone in order to create tension on and secure the first or damaged biological soft tissue. With reference to the biceps tendon 10, the hook 118 would engage the transverse ligament (not shown) or sheath 22 after the implant is secured to the tendon 10 in order to prevent a Popeye Sign. This engagement of the hook 118 with the sheath 22 can be similar to the engagement described above with reference to FIGS. 2A and 2B or the hook 118 can engage an interior of the sheath in order to prevent a Popeye Sign.

Figure 6A:
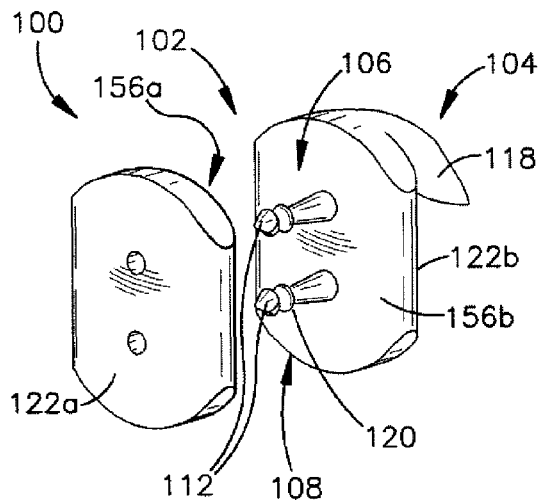
FIGS. 6A-C illustrate an embodiment of a biological soft tissue implant having cooperating parts that are snapably engageable where the implant is in different locking positions.
Figure 6B:
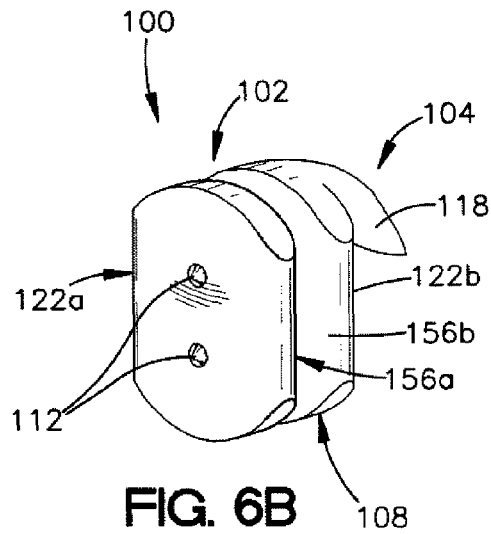
Figure 6C:
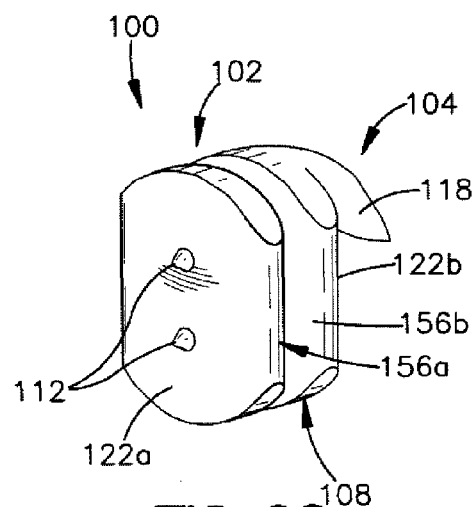
Figure 6D:
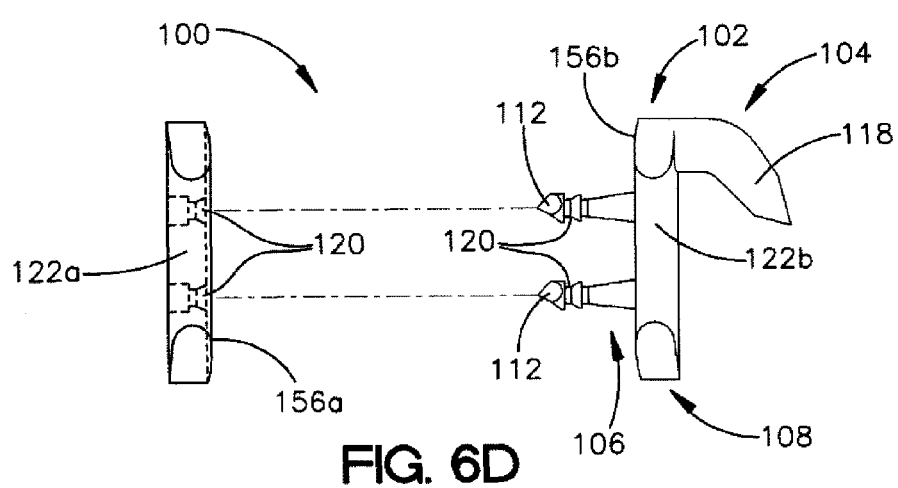
FIG. 6D is an elevation view of an elevation view of the cooperating parts of the implant of FIGS. 6A-C.

FIGS. 6A-D illustrate an alternate embodiment of the implant of FIGS. 5A-E. FIGS. 6A-C illustrate perspective views of a biological soft tissue implant 100 having a fastener 102 and anchor 104. The anchor 104 includes a hook 118. The fastener 102 includes cooperating parts 122a and 122b, which are snapably engageable opposing parts having gripping surfaces 156a and 156b with holes 114 on the gripping surfaces 156a. FIG. 6D is an elevation view of the cooperating parts 122a and 122b. The fastener 102 can be described as including both an engaging element 106 and a locking element 108. The engaging element 106 of the fastener 102 includes the cooperating parts 122a and 122b for trapping the biological soft tissue, the spikes 112 and the gripping surfaces 156a and 156b, as well as the holes 114. The spikes 112 may be configured with, for example, pyramidal tips as shown to facilitate penetration of the spikes 112 through biological soft tissue. The locking element 108 of the fastener 102 includes snap-fitting parts 120. In use, the implant 100 of FIGS. 6A-D is similar to that of the implant of FIGS. 5A-E.

Figure 7A:
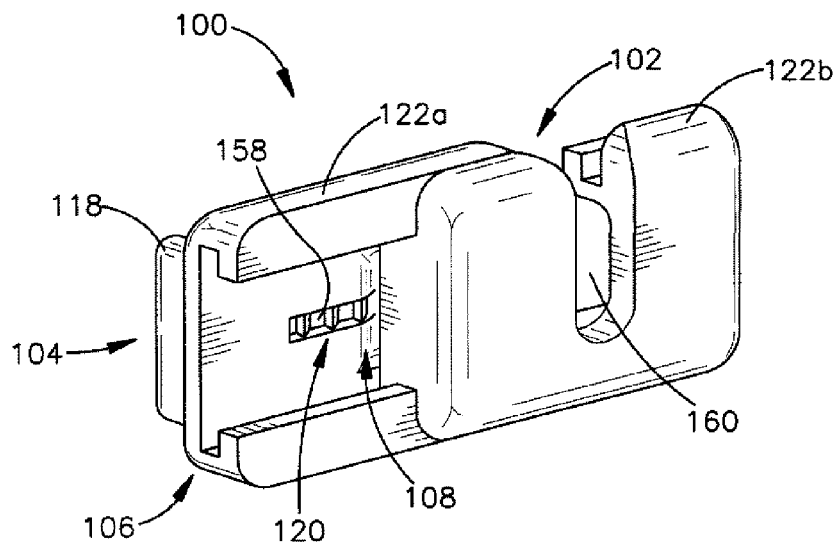
FIGS. 7A-C illustrate perspective views of the cooperating parts that are slidably engageable and shown at different positions of engagement.
Figure 7B:
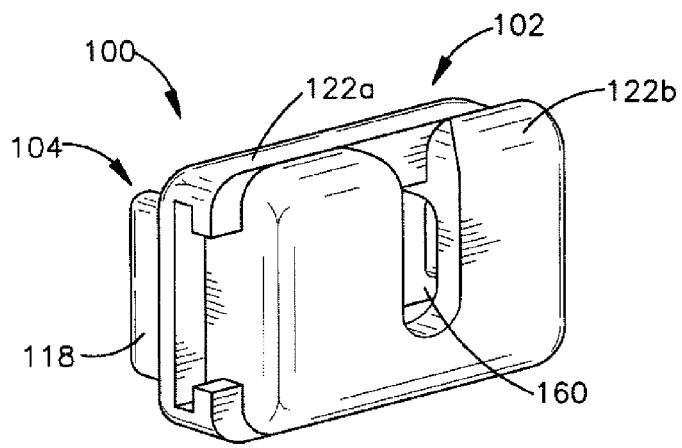
Figure 7C:
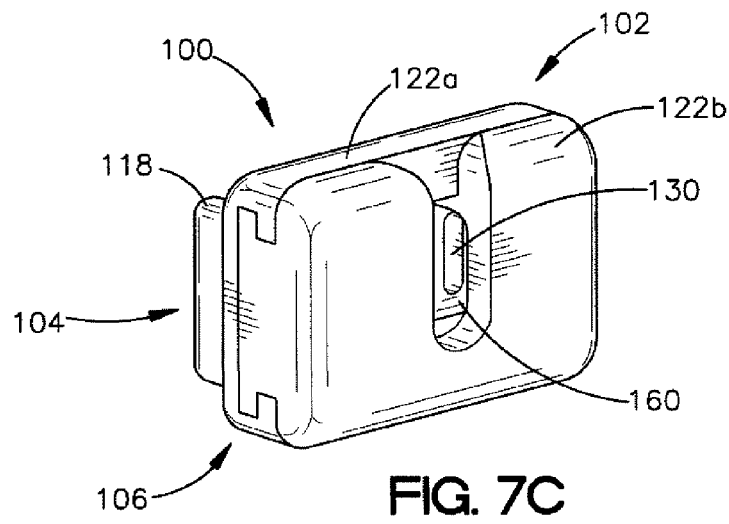
Figure 7D:
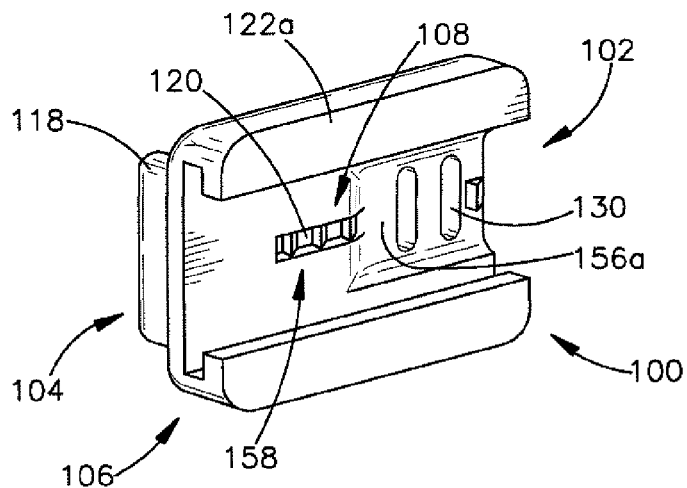
FIGS. 7D-E illustrate perspective views of one of the cooperating parts 122a of FIGS. 7A-C.
Figure 7E:
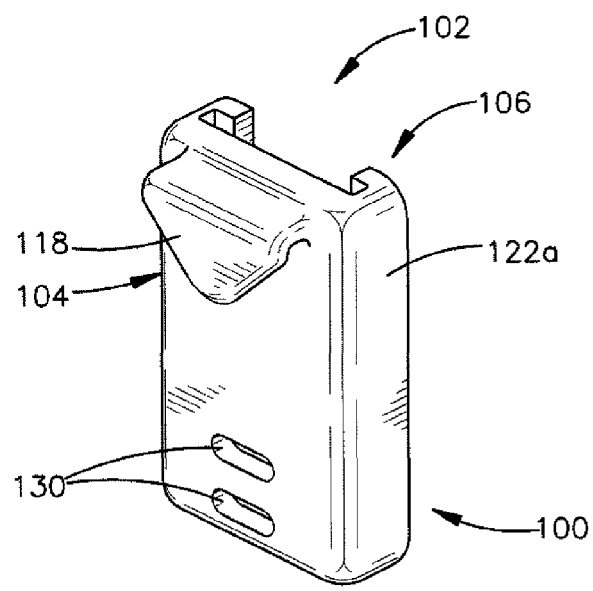
Figure 7F:
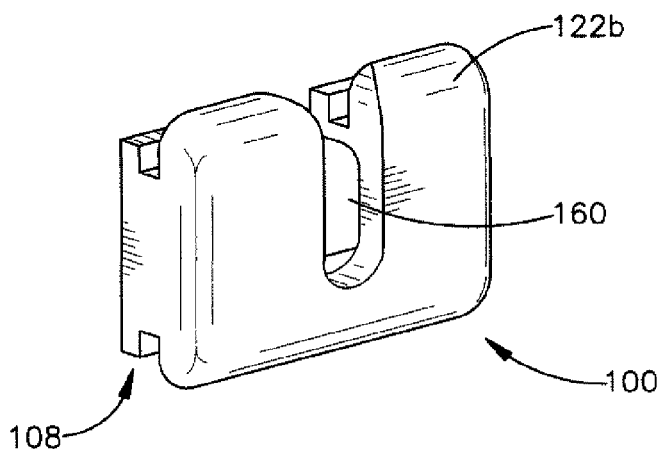
FIGS. 7F-G illustrate perspective views of the other cooperating part of FIGS. 7A-C.
Figure 7G:
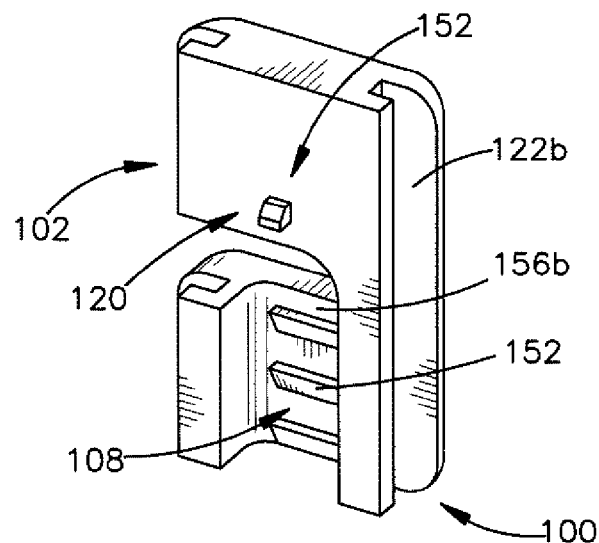
Figure 7H:
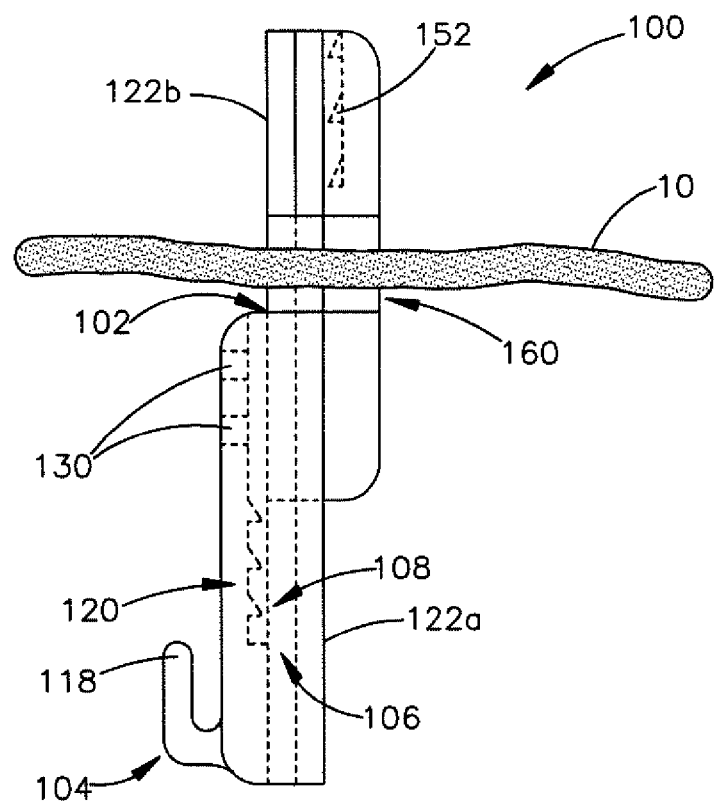
FIGS. 7H-J illustrate elevation views of the implant of FIGS. 7A-C engaging a biological soft tissue.
Figure 7I:
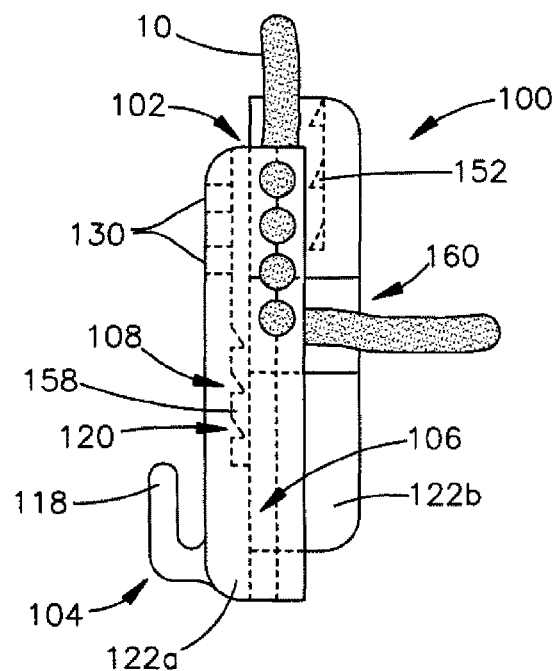
Figure 7J:
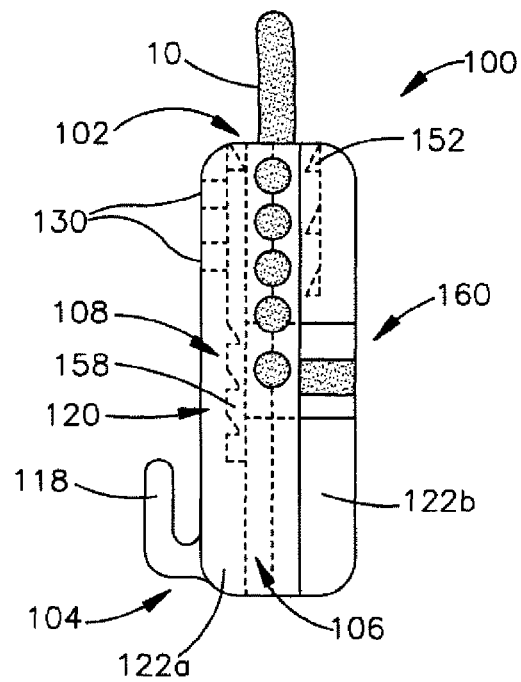

FIGS. 7A-J an embodiment of a biological soft tissue implant 100 having cooperating parts 122a and 122b that are slidably engageable parts. FIGS. 7A-C illustrate perspective views of the cooperating parts 122a and 122b at different positions of engagement. FIGS. 7D-E illustrate perspective views of the cooperating part 122a and FIGS. 7F-G illustrate perspective views of the cooperating part 122b. FIGS. 7H-J illustrate elevation views of the implant 100 engaging a biological soft tissue, such as a biceps tendon 10.

FIGS. 7A-J illustrate a biological soft tissue implant 100 having a fastener 102 and anchor 104. The anchor 104 includes a hook 118. The fastener 102 includes cooperating parts 122a and 122b that are slidably engageable opposing parts. The cooperating parts 122a and 122b have gripping surfaces 156a and 156b and the gripping surface 156a has slots 130. The fastener 102 can be described as including both an engaging element 106 and a locking element 108. The engaging element 106 includes the cooperating parts 122a and 122b for trapping the biological soft tissue, the gripping teeth 152 and the gripping surface 156 with slots 130. The locking element 108 includes snap-fitting parts 120, which includes teeth 152 and receivers 158.

As shown in FIGS. 7H-J, the fastener 102 engages the biological soft tissue, such as biceps tendon 10. First, the biological soft tissue 10 is placed in an aperture 160 of the cooperating parts 122b as shown in FIG. 7H. The cooperating parts 122a and 122b are then engaged as shown in FIG. 7I to engage and lock the biological soft tissue. When the cooperating parts 122a and 122b are brought together with the soft tissue 10 therebetween, the fastener 102 engages the biological soft tissue 10. Specifically, the gripping teeth 152 of the fastener 102 engage the soft tissue 10 as the cooperating parts 122a and 122b are slidably engaged. In addition, the gripping surface 156 and slots 130 help to engage the biological soft tissue 10.

Once engaged, the fastener 102 also includes a locking element 108. The locking element in the specific embodiment shown includes multiple locking positions as shown in FIGS. 7B-C. Thus, the fastener 102 can lock into multiple separate positions. The locking element 108 of the fastener 102 includes a protrusion, or teeth 152 and receivers 158 to allow the cooperating parts 122a and 122b to lock together after being slidably engaged. When the cooperating parts 122a and 122b are locked together, the biological soft tissue 10 is engaged and locked so that it is held securely between the cooperating parts 122a and 122b. As shown in FIG. 7J, tension on one side of the biological soft tissue 10 may be relieved such as by resection or severing the tissue 10 following engagement.

Figure 8A:
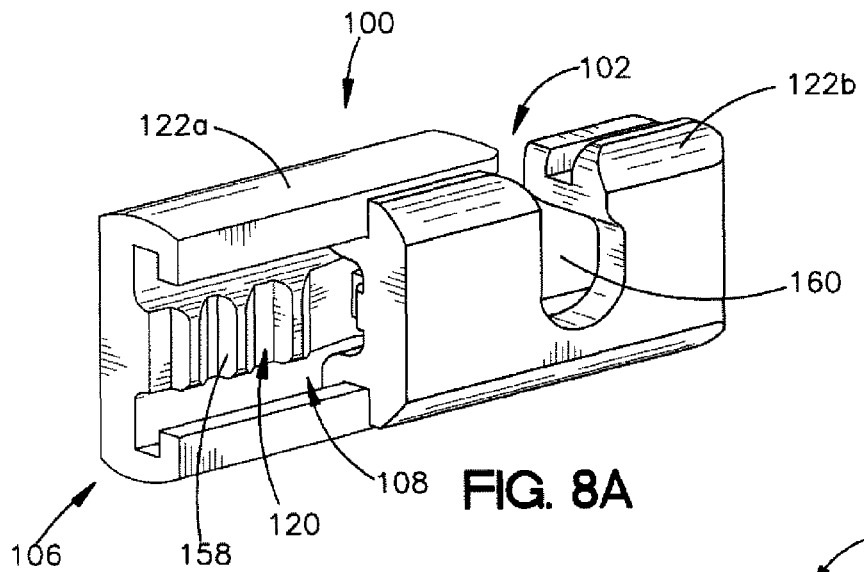
FIGS. 8A-C illustrate perspective views of the cooperating parts that are slidably engageable and shown at different positions of engagement.
Figure 8B:
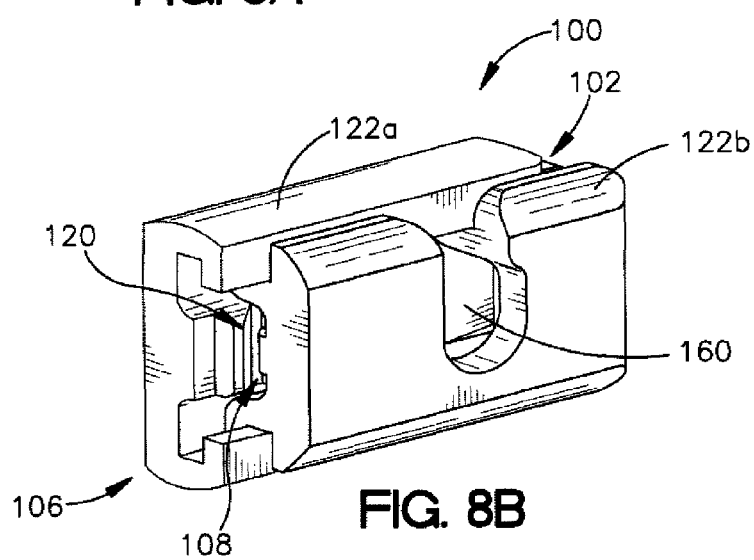
Figure 8C:
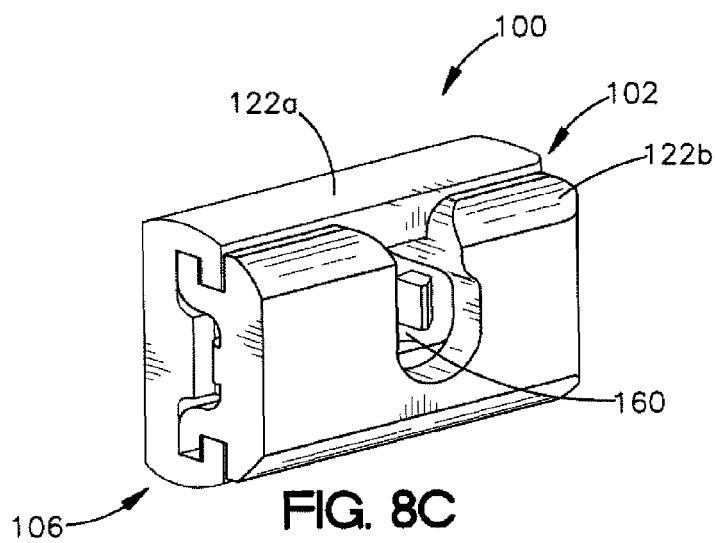
Figure 8D:
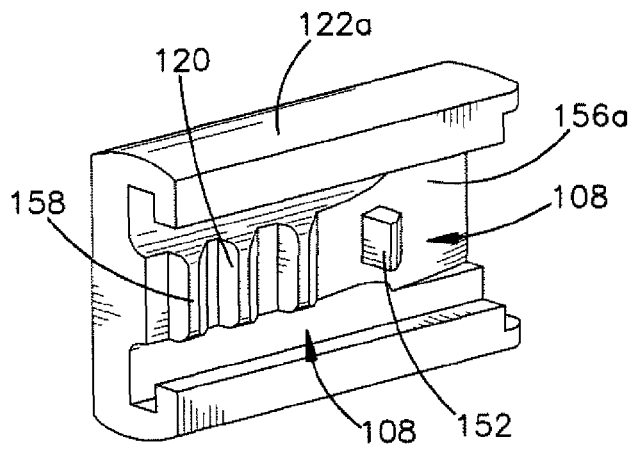
FIGS. 8D-E illustrate perspective views of one of the cooperating parts of FIGS. 8A-C.
Figure 8E:
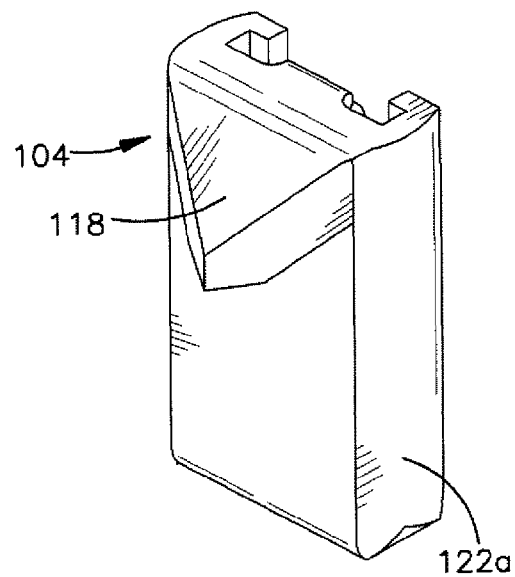
Figure 8F:
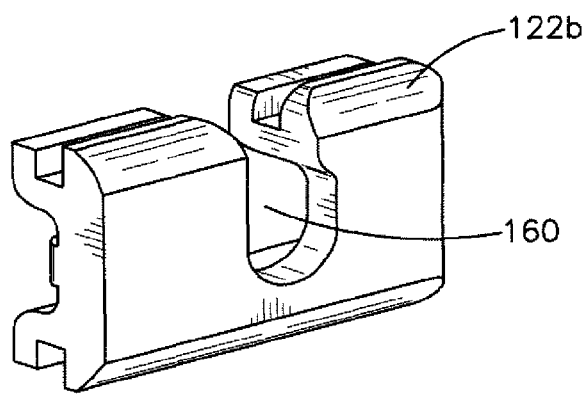
FIGS. 8F-G illustrate perspective views of the other cooperating part of FIGS. 8A-C.
Figure 8G:
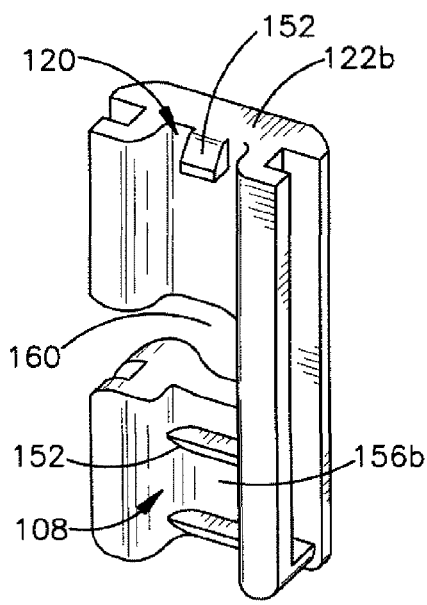
Figure 8H:
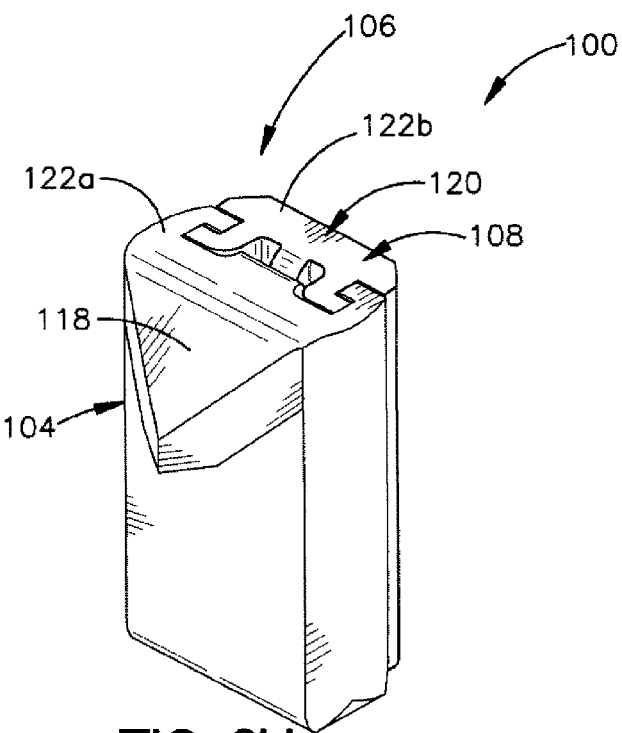
FIG. 8H illustrates another perspective views of the implant of FIGS. 8A-C showing the anchor.
Figure 8I:
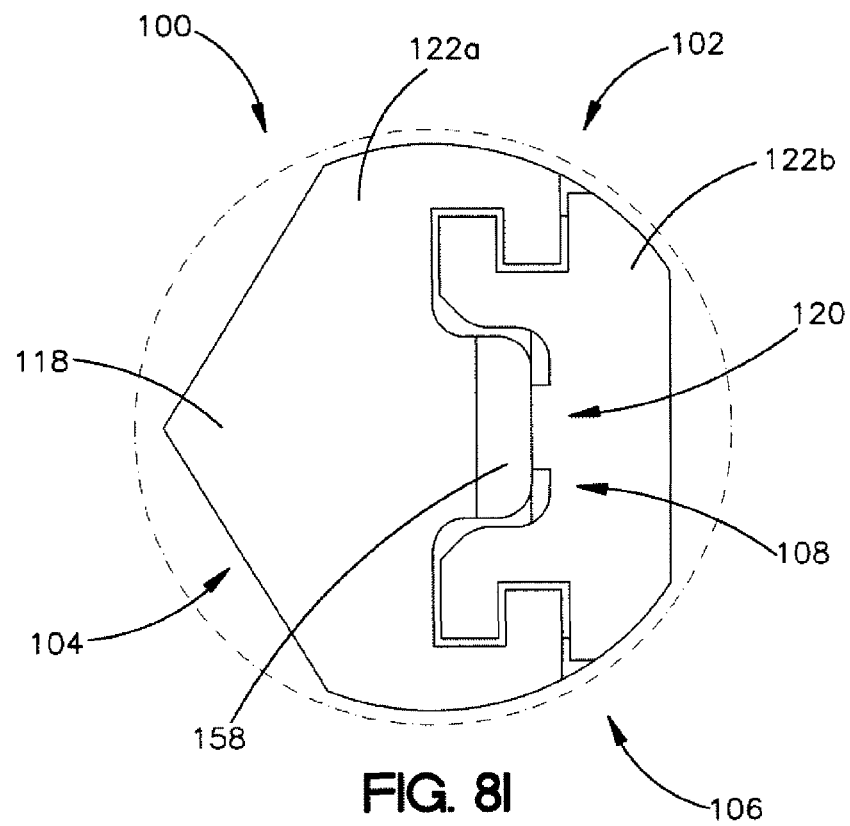
FIG. 8I is a plan view of the implant of FIGS. 8A-C as it might look inside a cannula.

FIGS. 8A-I illustrate another embodiment of a biological soft tissue implant 100 of FIGS. 7A-J. FIGS. 8A-C illustrate perspective views of the cooperating parts 122a and 122b at different positions of engagement. FIGS. 8D-E illustrate perspective views of the cooperating part 122a and FIGS. 8F-G illustrate perspective views of the cooperating part 122b. FIG. 8H is another perspective view of the implant 100 illustrating the anchor 104 and FIG. 8I is a plan view of the implant 100 as it might look inside a cannula. Preferably, the embodiments of FIGS. 7A-J and 8A-I are capable of being used for arthroscopic procedures and fit within the diameter of a cannula.

The implant 100 of FIGS. 8A-I is used in a manner similar to the implant 100 of FIGS. 7A-J and is similar in design and structure. The implant 100 of FIGS. 8A-J does not include slots 130 in a gripping surface 156. Also, the implant of FIGS. 8A-J includes larger and wider snap-fitting parts 120, both the tooth 152 and receivers 158. The fastener 102 includes cooperating parts 122a and 122b that are slidably engageable. The cooperating parts 122a and 122b have gripping surfaces 156a and 156b, respectively. The fastener 102 can be described as including both an engaging element 106 and a locking element 108. The engaging element 106 includes the cooperating parts 122a and 122b for trapping the biological soft tissue, the gripping teeth 152 and the gripping surface 156. The locking element 108 includes snap-fitting parts 120, which includes teeth 152 and receivers 158.

Figure 9A:
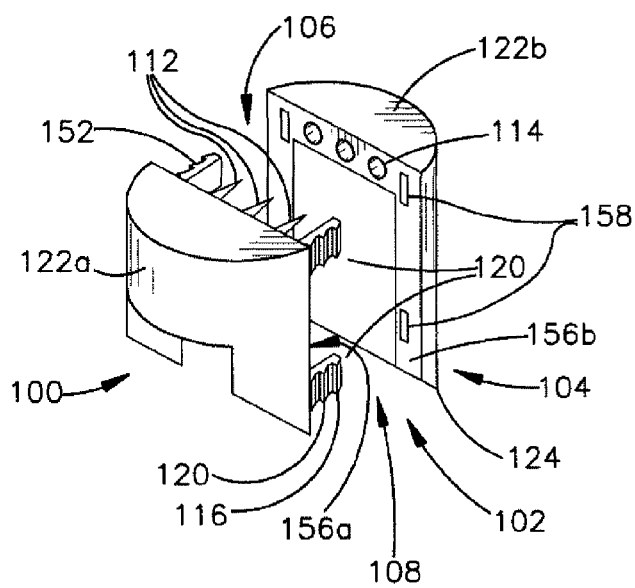
FIGS. 9A-D illustrate perspective view of a toggle implant in an open position and in three locked positions.
Figure 9B:
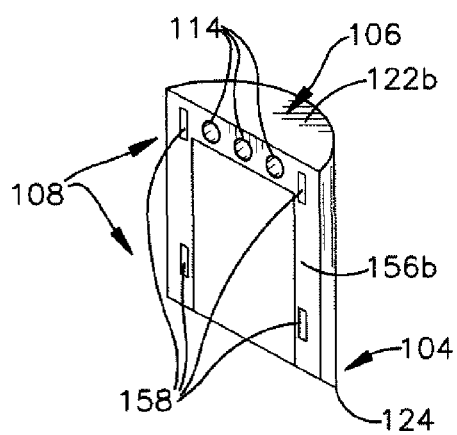
Figure 9C:
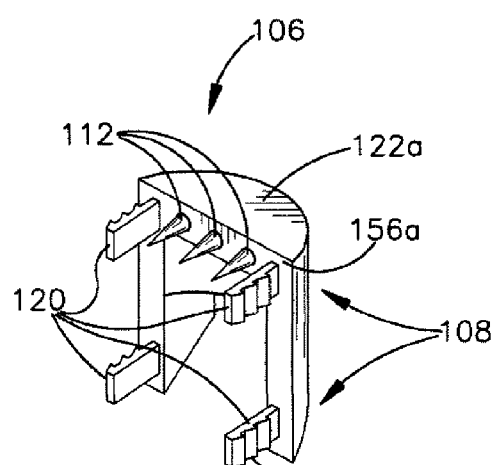
Figure 9D:
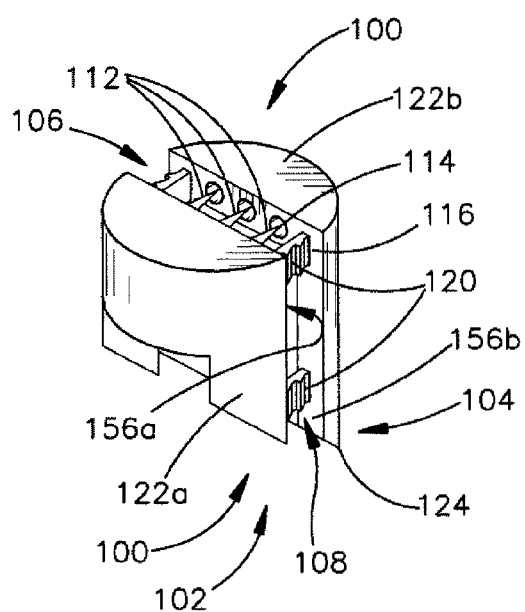
Figure 9E:
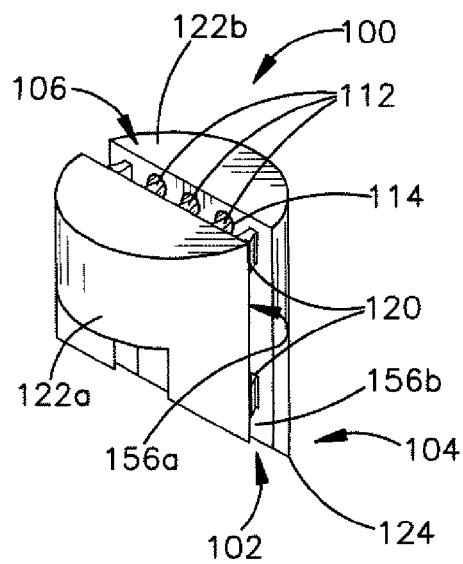
FIGS. 9E-F illustrate perspective views of cooperating parts of the implant of FIGS. 9A-C.
Figure 9F:
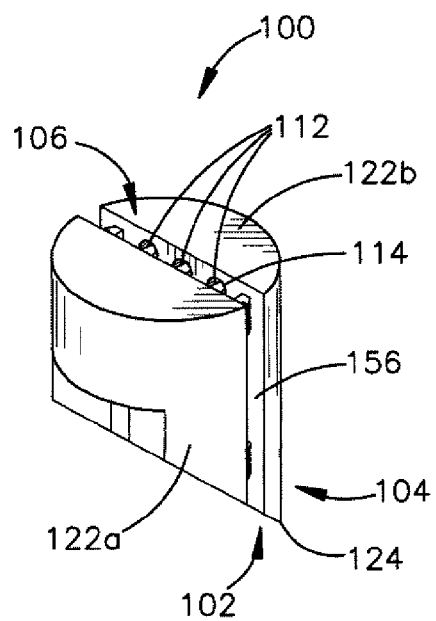
Figure 9G:
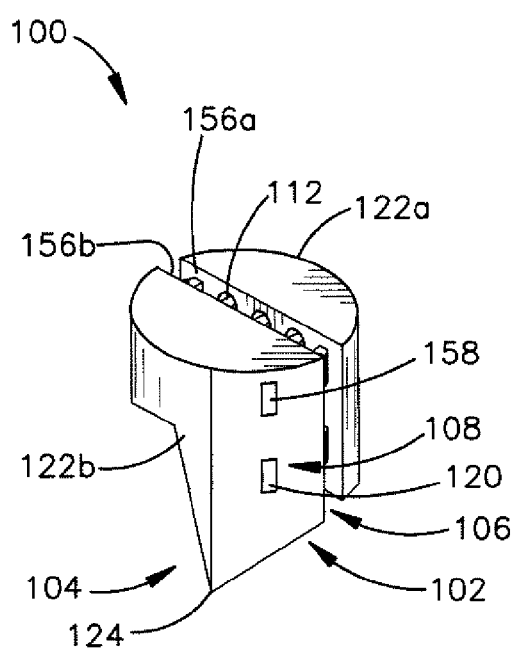
FIG. 9G illustrates a perspective view of the reverse side of the implant of the implant of FIGS. 9A-C.

FIGS. 9A-G illustrate one of the toggle embodiments of the present invention. FIGS. 9A-D illustrate perspective view of the implant 100 in an open position and in three locked positions. FIGS. 9E-F illustrate perspective views of cooperating parts 122a and 122b, respectively. FIG. 9G illustrates a perspective view of the reverse side of the implant. As can be seen in FIG. 9A, this toggle embodiment includes an implant 100 having a fastener 102 and an anchor 104. The anchor 104 includes a pointed end 124 configured to anchor when the implant 100 toggles, as explained below. The fastener 102 includes cooperating parts 122a and 122b that are snapably engageable. The cooperating parts 122a and 122b have gripping surfaces 156a and 156b, respectively. In addition, the gripping surface 156b has holes 114. The fastener 102 can be described as including both an engaging element 106 and a locking element 108. The engaging element 106 includes the cooperating parts 122a and 122b for trapping the biological soft tissue, the spikes 112, the gripping surfaces 156a and 156b and holes 114. The locking element 108 includes snap-fitting parts 120, which include teeth 152 and receivers 158. The snap-fitting parts 120 may include tabs having teeth or pawls as shown or any other conventional snap-fitting part that locks in place. Accordingly, the receivers 158 can be slots, holes, troughs, depressions or the like. The locking element 108 includes multiple locking positions as shown in FIGS. 9B-D. Thus, the fastener 102 can lock into three separate positions.

In use, the cooperating parts 122a and 122b, which are snapably engageable parts, trap the biological soft tissue. The spikes 112 are inserted through the biological soft tissue and into the corresponding holes 114 while the snap-fitting parts 120 are engaged and locked in place. In this manner, the spike/aperture engaging elements attach the fastener 102 to the tendon 10 while the snap-fitting locking parts 120 of the locking element 108 lock the implant 100 on the biological soft tissue.

While the fastener 102 is being attached to the tendon 10, the tendon 10 is preferably either still at least partially connected to the glenoid or if severed, is being held in place by the surgeon. Once the implant 100 is attached, the tendon 10 is released from the glenoid (if not previously severed) and the length of the tendon 10 that is located proximal to the implant 100 is resected. The implant 100 is then allowed to travel down so that the pointed end 124 of the anchor 104 engages with an inner surface of the sheath 22. Typically, the severed tendon will naturally be pulled down by the biceps muscle 16. The force of the biceps muscle 16 pulling on the severed tendon 10 operates to cause the implant 100 to rotate or toggle so that with increased tension, the pointed end 124 will become securely engaged with the inner surface of the sheath 22, and with an increase in tension, the tendon 10 will become even more securely engaged. In other words, as tension increases on the implant 100, the pointed end 124 will rotate in an upwards motion and push or dig further into the sheath 22 making a secure anchoring of the implant 100 in order to prevent a Popeye Sign.

Figure 10A:
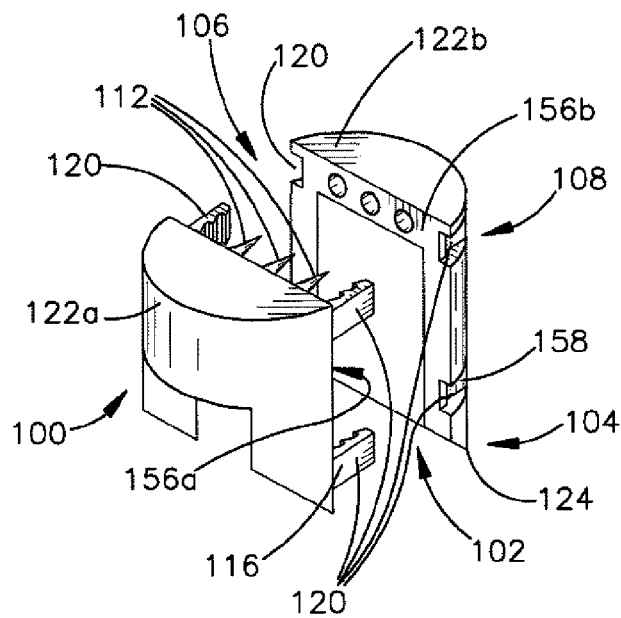
FIGS. 10A-D illustrate perspective view of a toggle implant in an open position and in three locked positions.
Figure 10B:
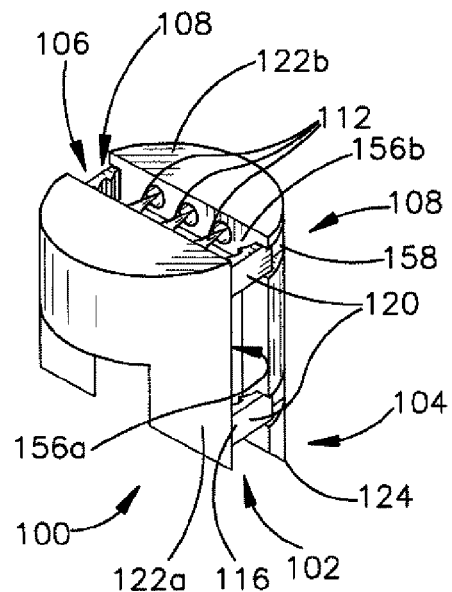
Figure 10C:
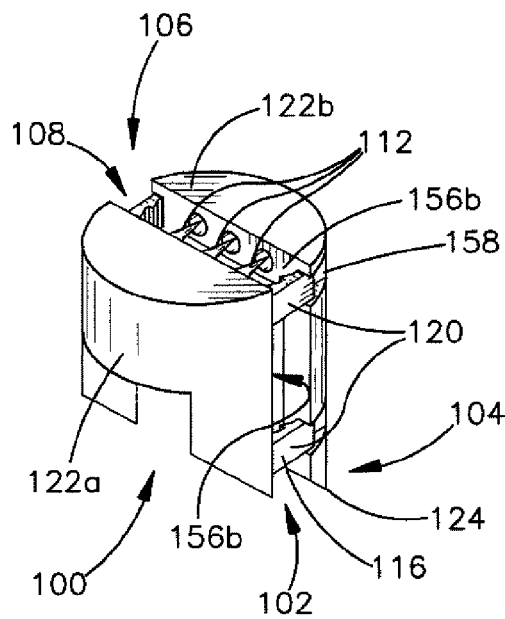
Figure 10D:
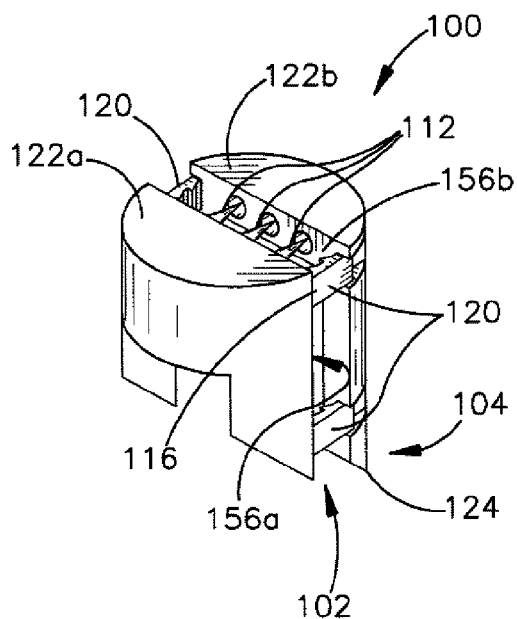
Figure 10E:
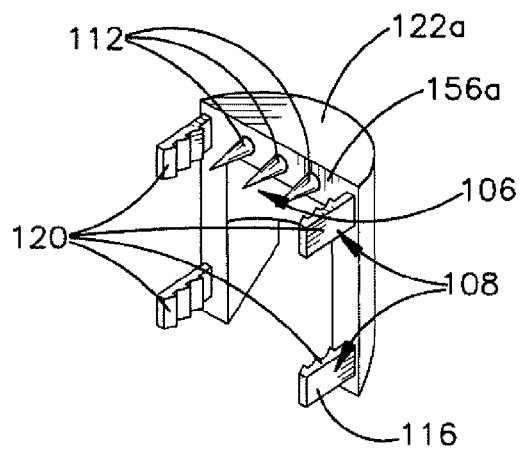
FIGS. 10E-F illustrate perspective views of cooperating parts of the implant of FIGS. 10A-C.
Figure 10F:
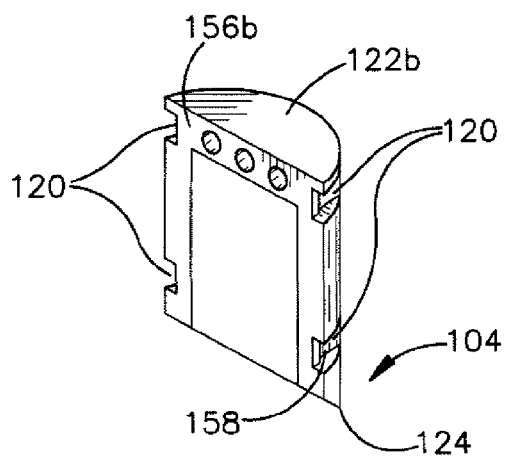
Figure 10G:
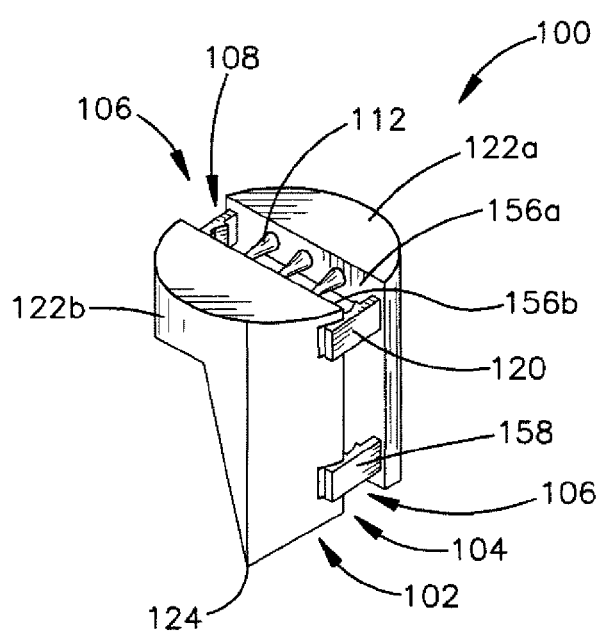
FIG. 10G illustrates a perspective view of the reverse side of the implant of the implant of FIGS. 10A-C.
Figure 11A:
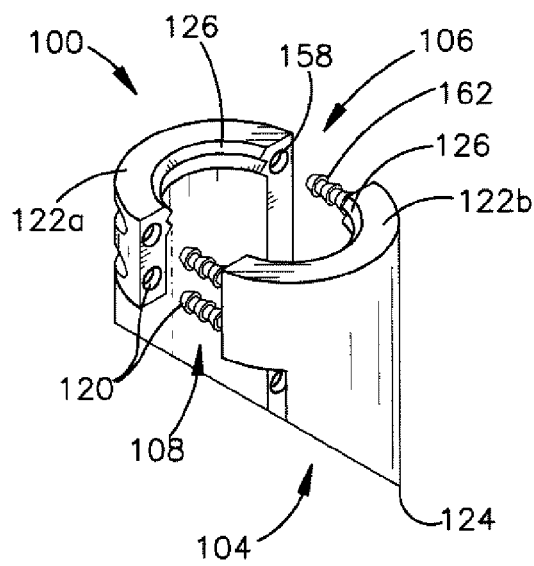
FIGS. 11A-D illustrate perspective view of a toggle implant in an open position and in three locked positions.
Figure 11B:
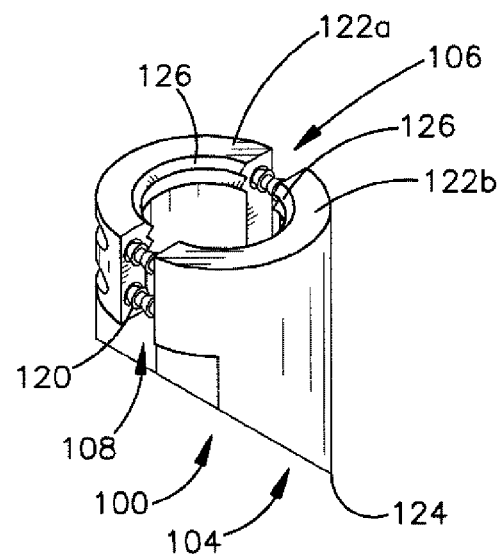
Figure 11C:
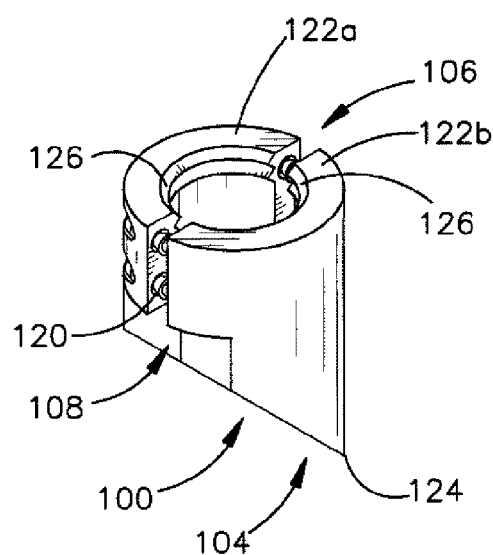
Figure 11D:
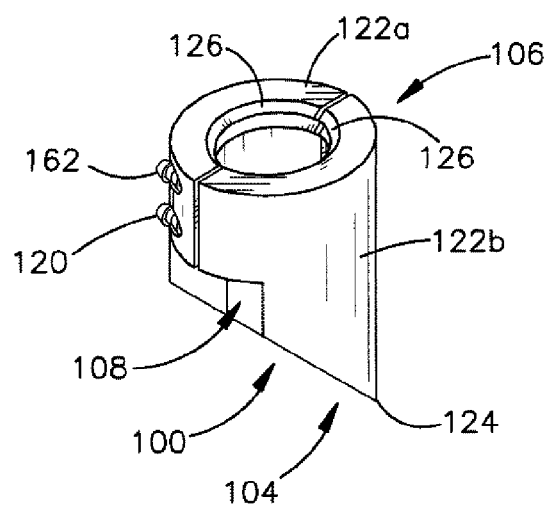
Figure 11E:
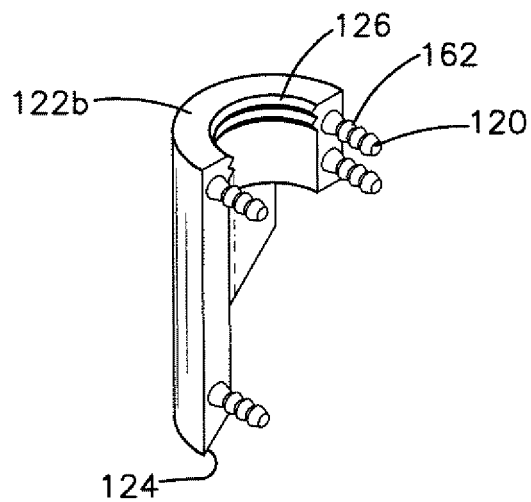
FIGS. 11E-F illustrate perspective views of cooperating parts of the implant of FIGS. 11A-C.
Figure 11F:
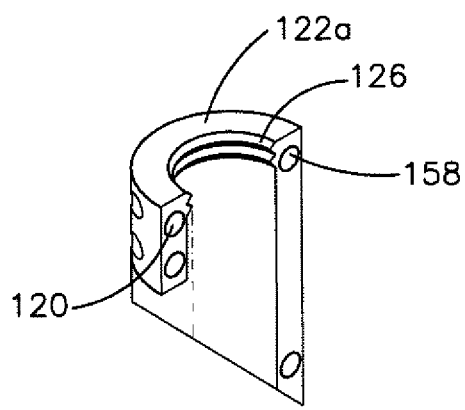
Figure 11G:
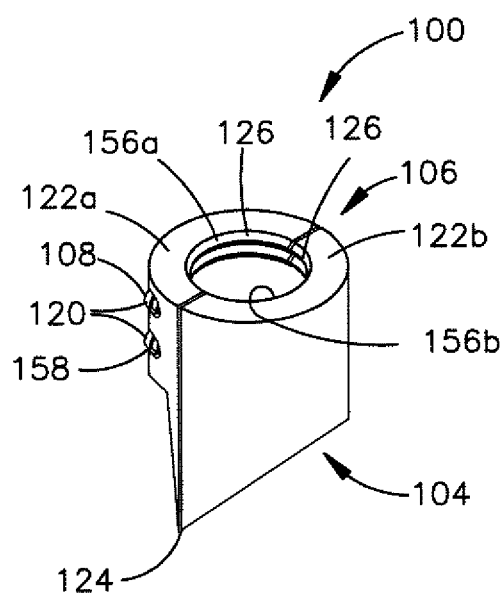
FIG. 11G illustrates a perspective view of the reverse side of the implant of the implant of FIGS. 11A-C.
Figure 12A:
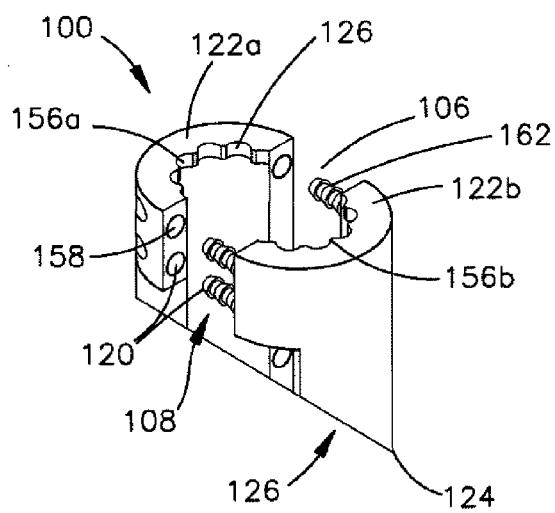
FIGS. 12A-F illustrate another embodiment of a toggle biological soft tissue implant.
Figure 12B:
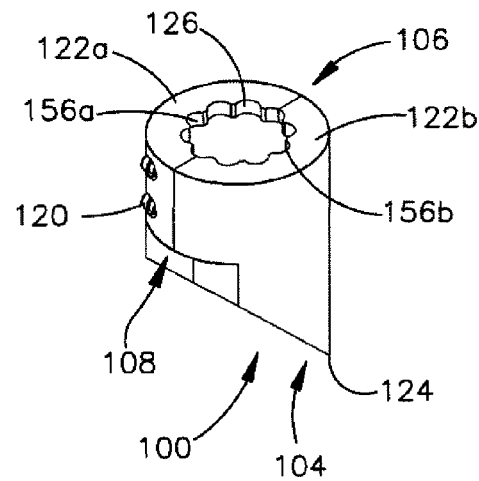
Figure 12C:
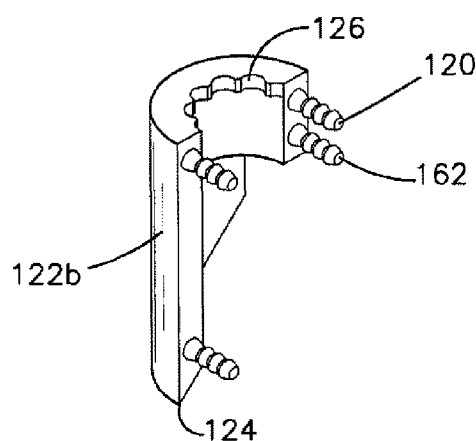
Figure 12D:
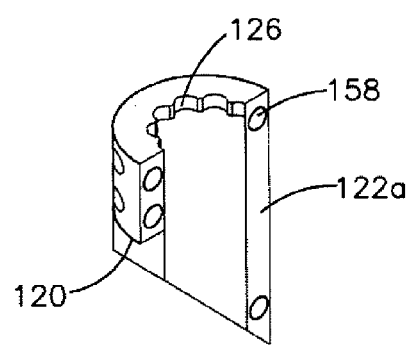
Figure 12E:
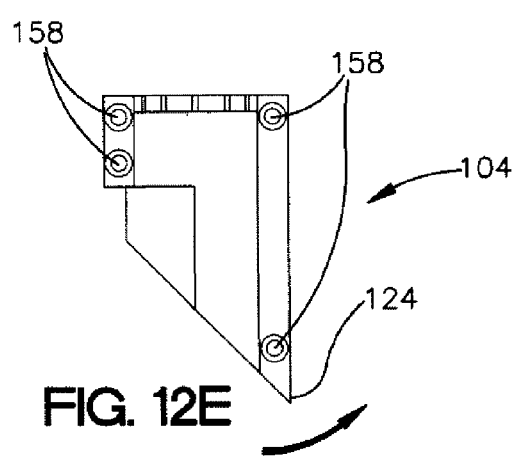
Figure 12F:
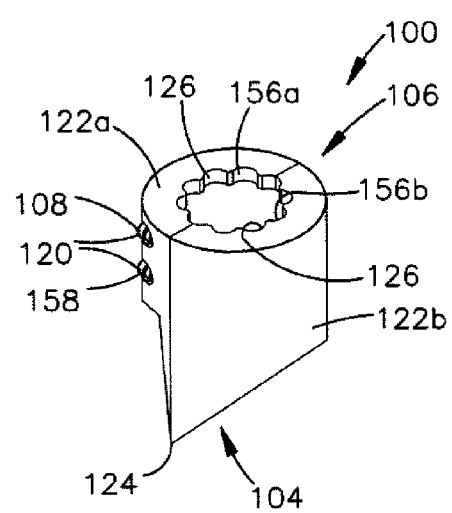
Figure 13A:
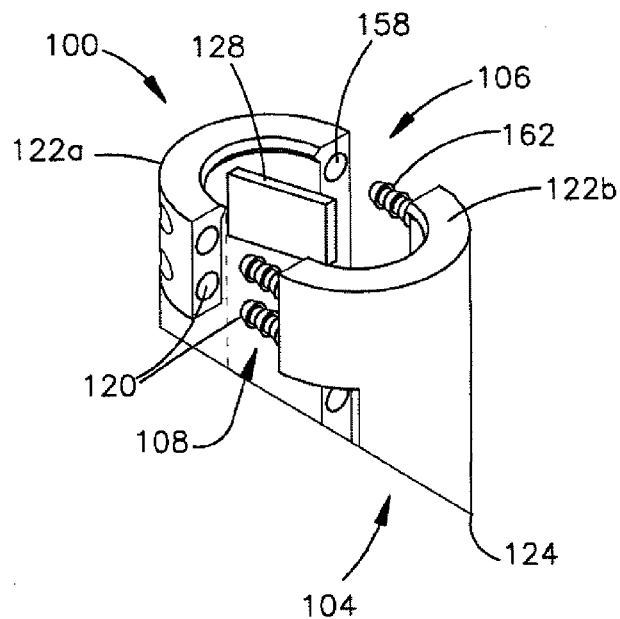
Figure 13B:
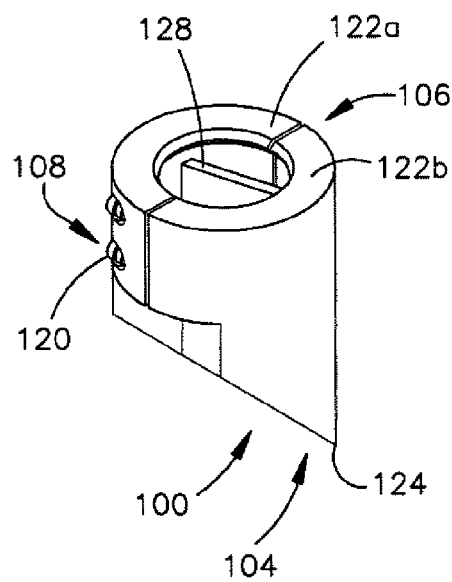
Figure 13C:
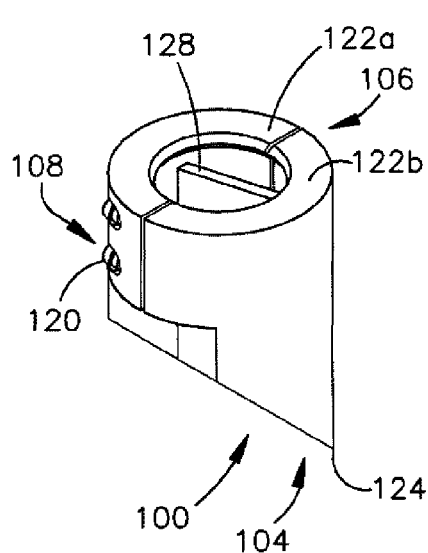
Figure 13D:
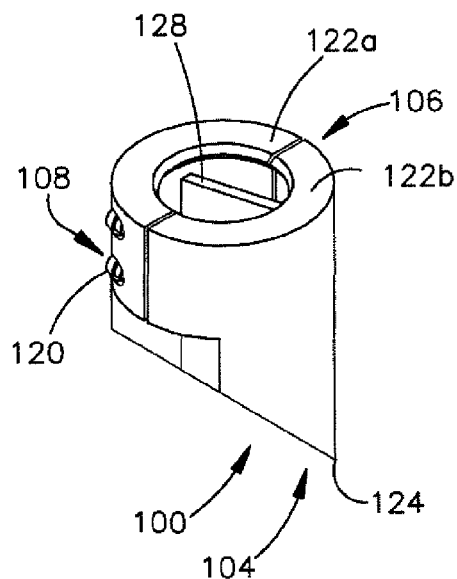
Figure 14A:
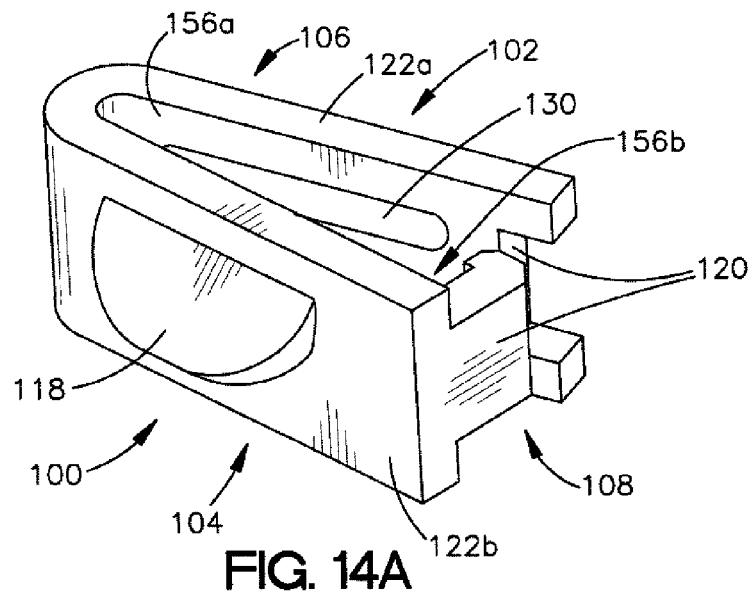
FIGS. 14A-B illustrate perspective views of an embodiment of a clip-type biological soft tissue implant.
Figure 14B:
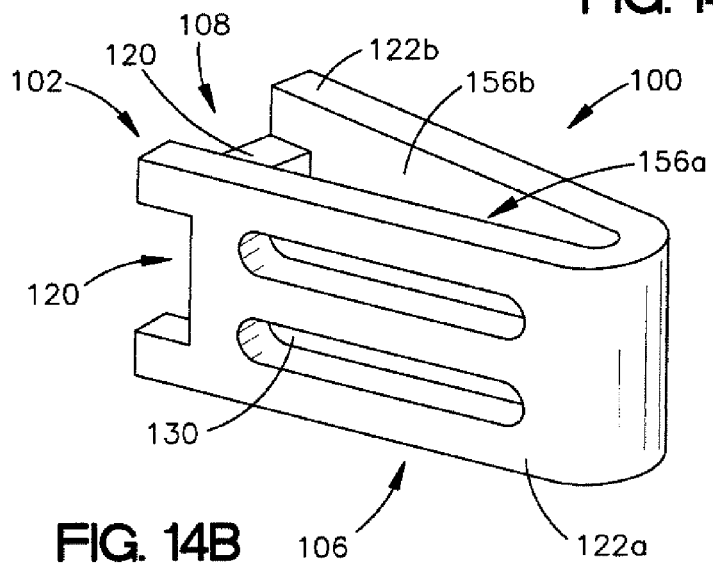
Figure 14C:
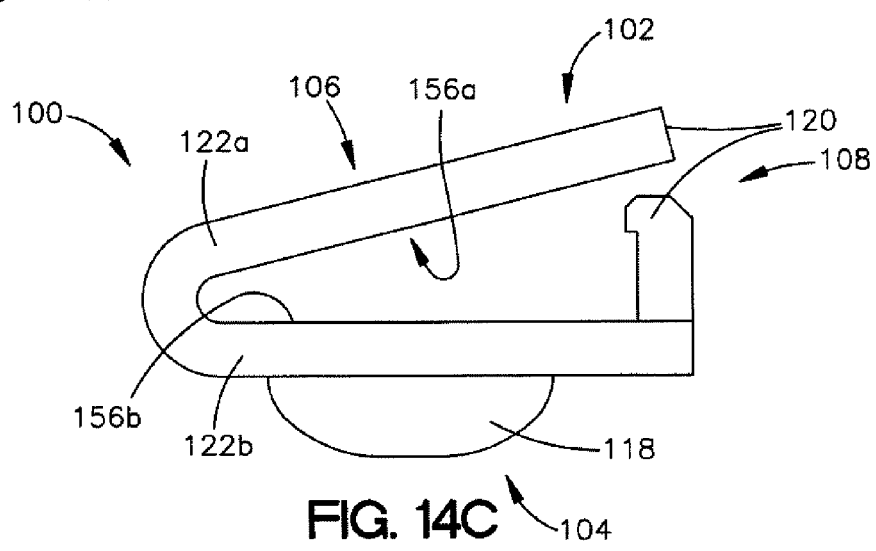
FIG. 14C illustrates a plan view of the implant of the embodiment of FIGS. 14A-B.

FIGS. 10A-G illustrate an alternative embodiment of the implant of FIGS. 9A-G. FIGS. 10A-G illustrate one of the toggle embodiments of the present invention. FIGS. 10A-D illustrate perspective views of the implant 100 in an open position and in three locked positions. FIGS. 10E-F illustrate perspective views of cooperating parts 122a and 122b, respectively. FIG. 10G illustrates a perspective view of the reverse side of the implant. The implant 100 of FIGS. 10A-G is used just as the implant of FIGS. 9A-G and is similar in design and structure, except that the snap-fitting parts 120 of the implant of FIGS. 10A-G are different than those of the implant of FIGS. 9A-G. In this embodiment, the snap-fitting parts 120 also include teeth 152 that engage a retaining surface 154, rather than the holes or slots of FIGS. 9A-G. The locking element 108 includes multiple locking positions as shown in FIGS. 10B-D.

FIGS. 11A-G and 12A-F illustrate additional alternative embodiments of the implant of FIGS. 9A-G. The implants 100 of 11A-G and 12A-F are used just as the implant of FIGS. 9A-G and are similar in design and structure. The anchor 104 includes a pointed end 124 configured to anchor when the implant 100 toggles. The fastener 102 includes parts 122a and 122b that are snapably engageable and have gripping surfaces 156a and 156b with ridges 126 on the gripping surfaces 156a and 156b. For FIGS. 11A-G, the ridges 126 run vertically, whereas in FIGS. 12A-F, the ridges 126 run horizontally. The fastener 102 can be described as including both an engaging element 106 and a locking element 108. The engaging element 106 includes the cooperating parts 122a and 122b for trapping the biological soft tissue and the gripping surfaces 156a and 156b with ridges 126. The locking element 108 includes snap-fitting parts 120, which include pins 162 and receivers 158. FIGS. 11A-G and FIGS. 12A-F include a locking element 108 that has multiple locking positions.

FIGS. 13A-G illustrate another alternative embodiment of the implant of FIGS. 9A-G. The implant 100 of FIGS. 13A-G is used just as the implant 100 of FIGS. 11A-G and is similar in design and structure. In this embodiment, the engaging element 106 of the fastener 102 includes a gripping beam 128 as well as a single vertical ridge 126.

Figure 15C:
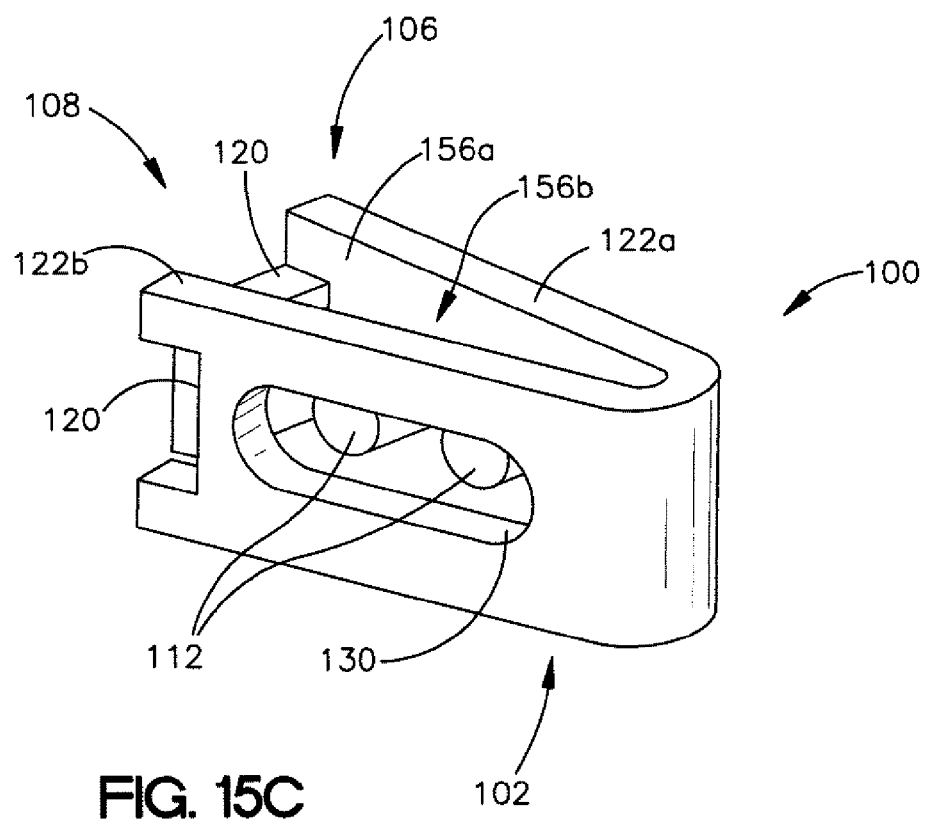
Figure 15D:
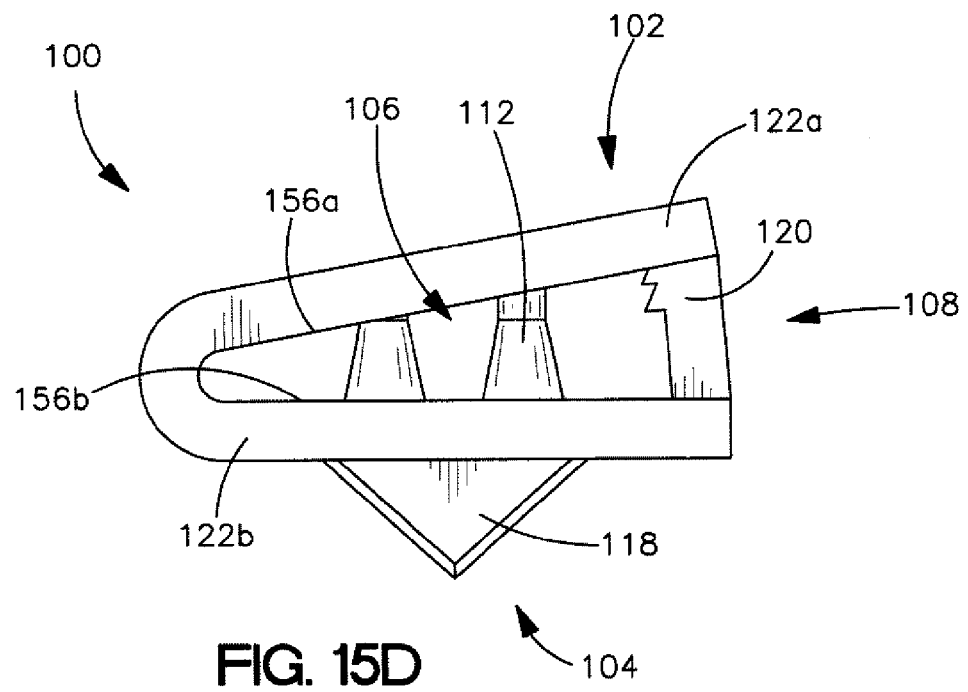
FIG. 15D illustrates a plan view of another embodiments of clip-type biological soft tissue implant.

FIGS. 14A-C and 15A-D all illustrate alternative clip embodiments of the present invention. Each of the embodiments includes cooperating parts 122a and 122b that are snapably engageable. Each of the embodiments also includes an implant 100 having a fastener 102 and anchor 104. The anchor 104 includes a hook 118 in FIGS. 14A-C, and FIG. 15B. FIG. 15A illustrates a flap 116 and FIGS. 15C-D can have either a hook 118 or flap 116. The fasteners 102 include cooperating parts 122a and 122b that are snapably engageable and include gripping surfaces 156a and 156b, respectively. The fastener 102 can be described as including both an engaging element 106 and a locking element 108. The engaging element 106 includes the cooperating parts 122a and 122b for trapping the biological soft tissue, and the gripping surface 156. For FIGS. 14A-C, the engaging element also includes slots 130. For FIG. 15C, the engaging element also includes spikes 112. The locking element 108 includes snap-fitting parts 120.

Figure 16A:
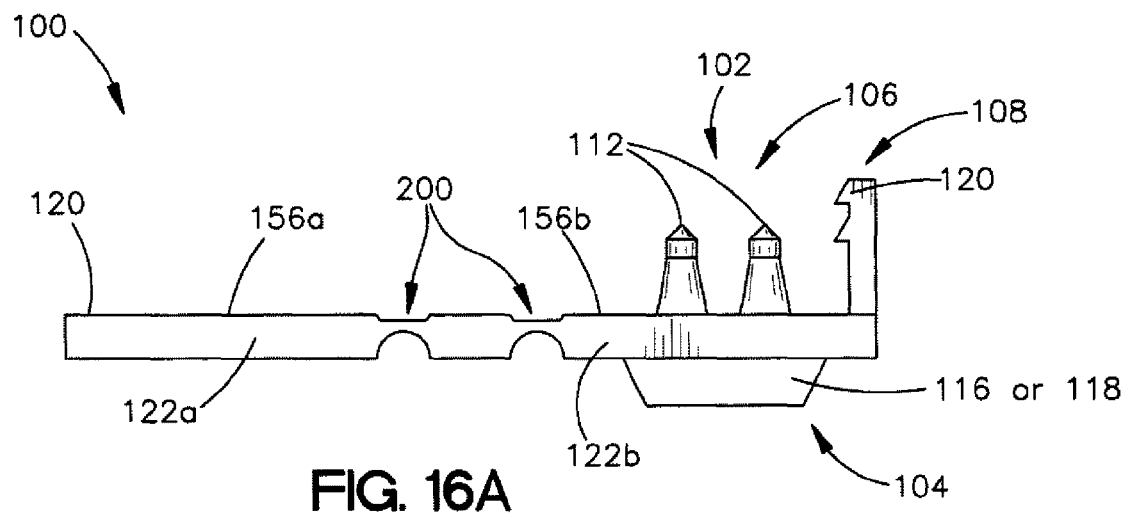
FIGS. 16A-B illustrate front elevation views of embodiments of clip-type biological soft tissue implants with living hinges.
Figure 16B:
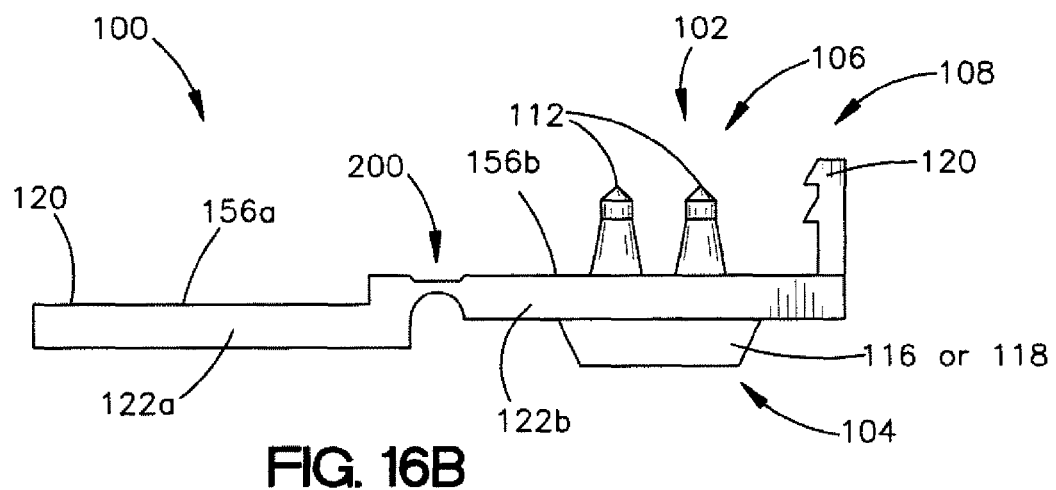

FIGS. 16A-B are two similar embodiments of living hinge embodiments of the present invention. Each of the embodiments includes cooperating parts 122a and 122b that are snapably engageable and separated by at least one living hinge 200. Each of the embodiments also includes an implant 100 having a fastener 102 and anchor 104. The anchor 104 includes a flap 116 or hook 118. The fasteners 102 include cooperating parts 122a and 122b having a gripping surfaces 156a and 156b, respectively. The fastener 102 can be described as including both an engaging element 106 and a locking element 108. The engaging element 106 includes the cooperating parts 122a and 122b for trapping the biological soft tissue, gripping surfaces 156a and 156b, and spikes 112. The locking element 108 includes snap-fitting parts 120 that allow the implant 100 to have two locking positions.

Figure 17A:
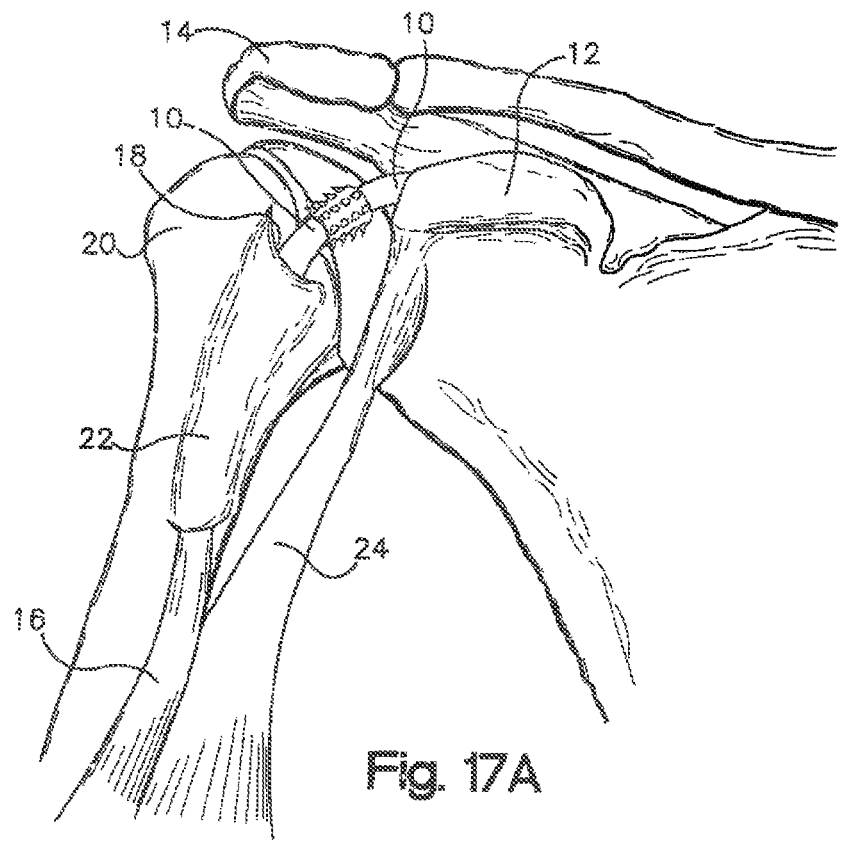
FIG. 17A is similar to FIG. 2A and illustrates a biological soft tissue implant attached to the biceps tendon in accordance with the present invention.
Figure 17B:
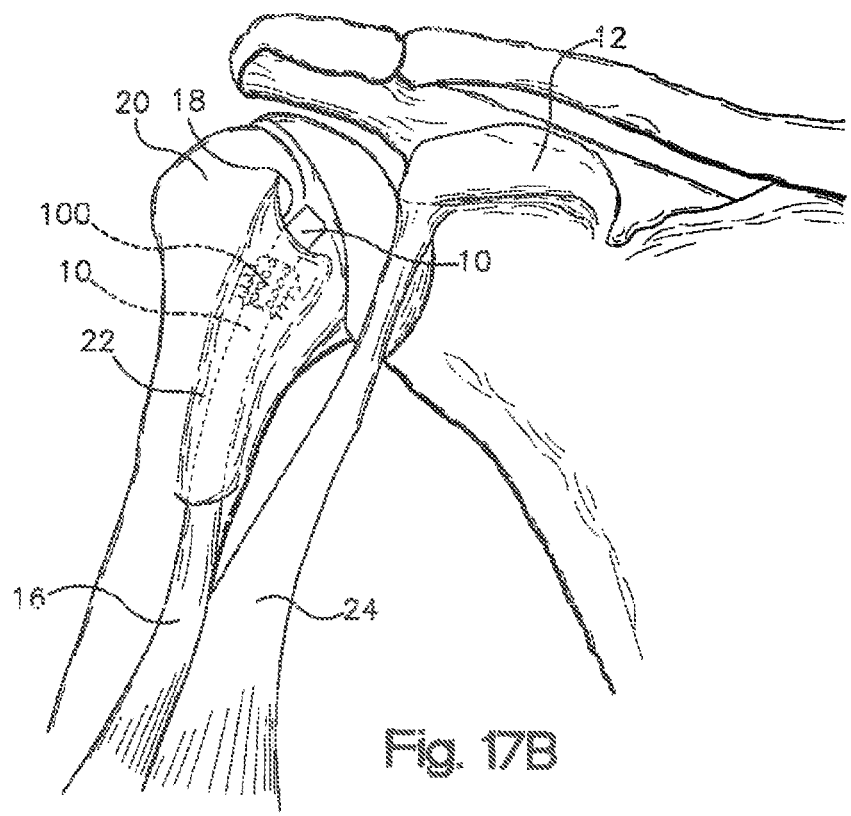
FIG. 17B is similar to FIG. 17A and shows the biological soft tissue implant of 17A anchoring and interacting with the bicipital sheath as the biceps tendon retracts.

FIG. 17A shows another embodiment of an implant 100 according to the present invention that is attached to a damaged biological soft tissue 10. The implant 100 is configured such that once the damaged biologic soft tissue 10 is severed, as shown in FIG. 17B, the implant 100 interacts with a second biological soft tissue (or a bone) to prevent the severed biologic soft tissue 10 from retracting beyond a predetermined position. In the specific example of FIGS. 17A-B, the tendon 10 is severed at the glenoid, such as during a tenotomy. Without the aid of the implant 100 of the present invention, the tendon 10 may retract down through the bicipital sheath 22. This causes what is known as the Popeye Sign condition, as described above.

If the implant 100 is attached to the biceps tendon 10 prior to severing the tendon 10, however, the implant 100 will interact with the bony bicipital groove 18 and the tissue of the bicipital sheath 22, thereby capturing the biceps tendon 10 within the bicipital groove 18 and causing tension on the tendon 10 between the implant 100 and the bicep 16. This prevents the tendon 10 from retracting beyond a predetermined position. This predetermined position may be any position that prevents an undesired effect associated with severing the biological soft tissue, such as a Popeye Sign. After capturing the tendon 10, the implant 100 places tension on one side of the biological soft tissue that is less than the tension placed on the biological soft tissue on the other side of the biological soft tissue implant 100. Moreover, any retraction of the first biological tissue further increases the interaction of the biological soft tissue implant 100 with the second biological soft tissue or the bony tissue. In other words, as the first biological tissue retracts, the implant 100 strengthens its connection or attachment with or to the second biological tissue.

It should be noted that the bicipital sheath 22 boundaries include the transverse ligament and the bony bicipital groove 18. Therefore, the implant 100 may be configured so that it is of a greater size in one dimension than in another (i.e. it is in a shape other than round). Thus, when the implant 100 engages the bicipital groove 18, it may tend to self-align by action of the bicipital groove 18, and thus engage the boundaries of the sheath 22. Thus, fixation of the implant 100 may be achieved by engagement with the bicipital tunnel bounded by the bicipital sheath 22 and the bony bicipital groove 18.

Figure 18:
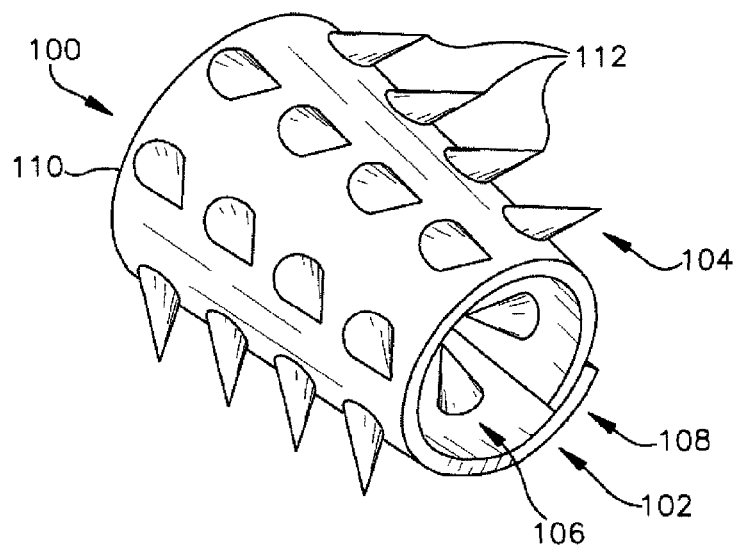
FIG. 18 illustrates a perspective view of the biological soft tissue implant of FIGS. 17A-B.

FIG. 18 illustrates the specific embodiment of the implant of FIGS. 17A-B. The implant 100 includes a fastener 102 and anchor 104. The anchor 104 is a series of spikes 112. The fastener 102 of the implant 100 is attached to the biceps tendon 10 as described above. The fastener 102 includes a retaining ring 110 with spikes 112 and a gripping surface 156. The retaining ring 110 of the fastener 102 is placed about the tendon 10 and squeezed or crimped to engage the biological soft tissue so that the spikes 112 are forced to engage the biological soft tissue and further secure the fastener 102 with the biological soft tissue. The spikes 112 may be forced into the biological soft tissue or even penetrate through the biological soft tissue to provide a secure connection or anchorage of the implant 100.

Figure 19A:
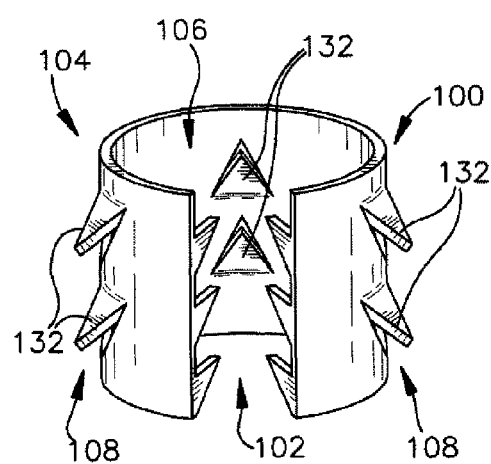
FIGS. 19A-B illustrate perspective views of another embodiment of the biological soft tissue implant alone and installed about a biological soft tissue.
Figure 19B:
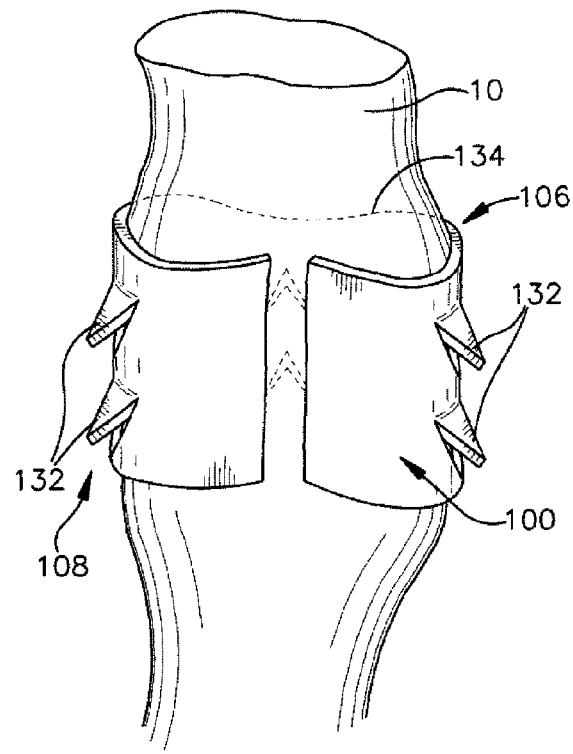

FIGS. 19A-B illustrate another alternative embodiment of the implant 100 alone and attached to a biological soft tissue. The implant 100 is similar to that of FIG. 18A except that the fastener 102 and anchor 104 each include barbs 132 instead of spikes 112.

Figure 20A:
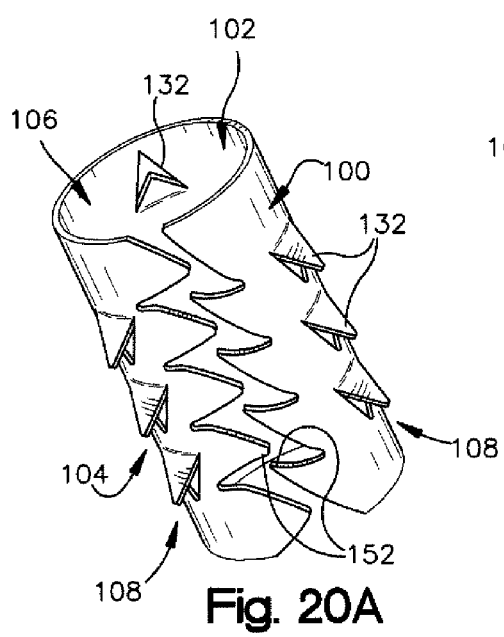
FIGS. 20A-B illustrate perspective views of another embodiment of the biological soft tissue implant alone and installed about a biological soft tissue.
Figure 20B:
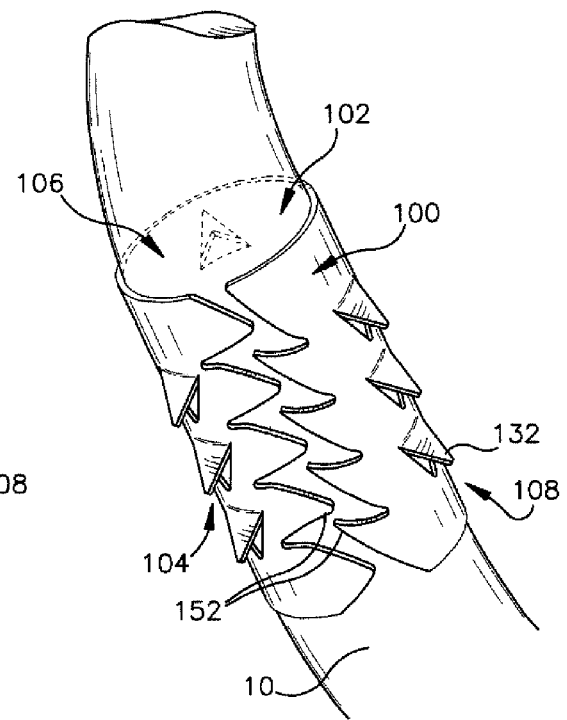

FIGS. 20A-B illustrate another alternative embodiment of the implant alone and attached to a biological soft tissue. The implant 100 is similar to that of FIG. 19-A-B except that the retaining ring includes interdigitating teeth 152 along the seam of the retaining ring 110.

Figure 21A:
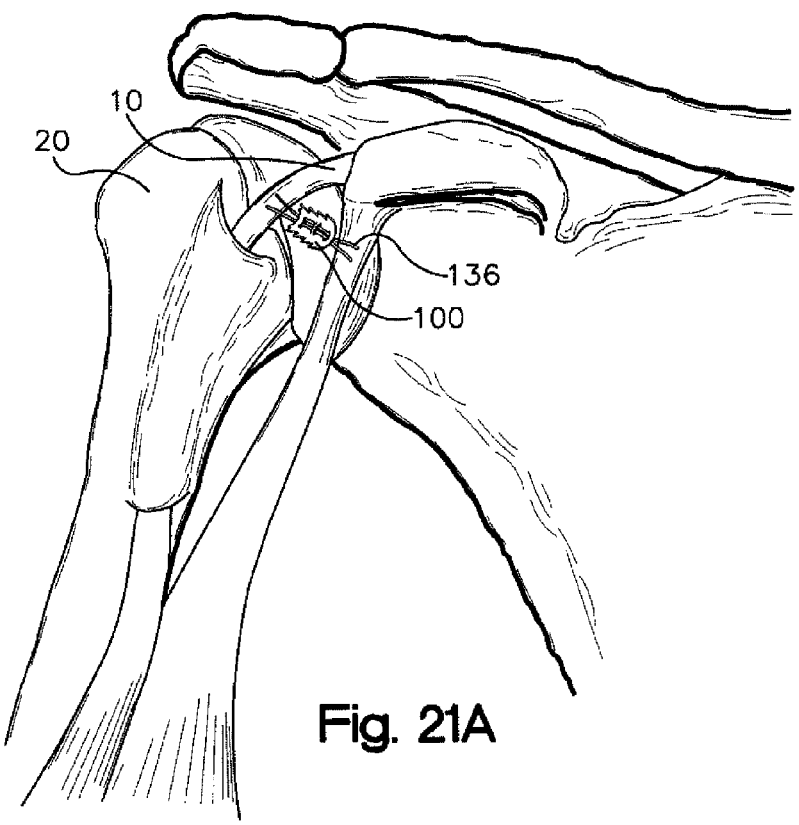
FIGS. 21A-D illustrate perspective views of another biological soft tissue implant attached to the biceps tendon and the procedure associated therewith in accordance with the present invention.
Figure 21B:
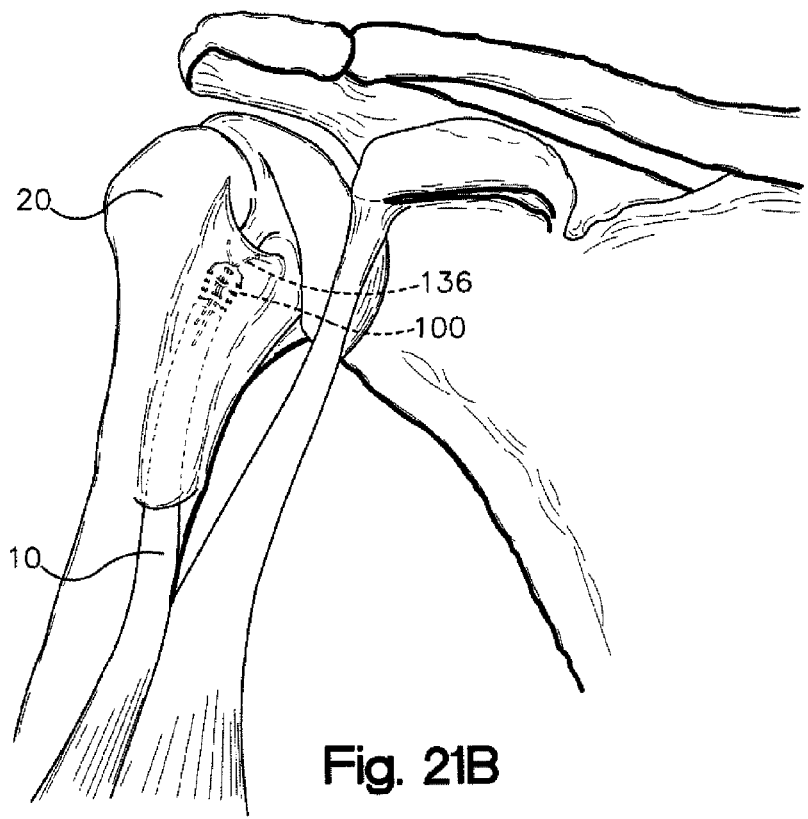
Figure 21C:
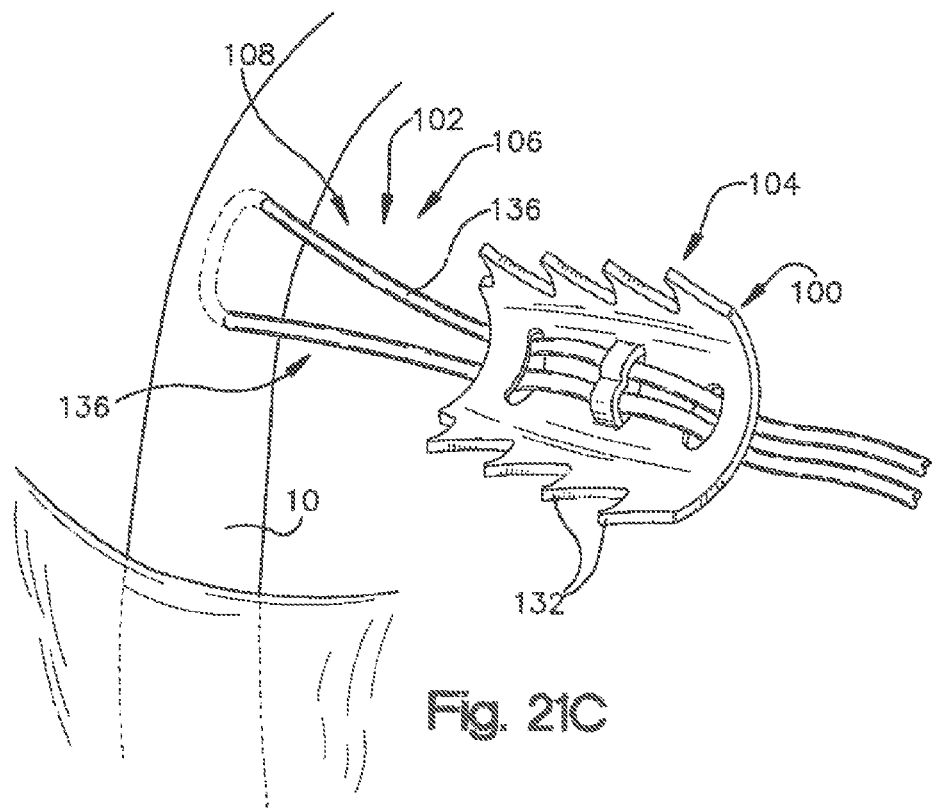
Figure 21D:
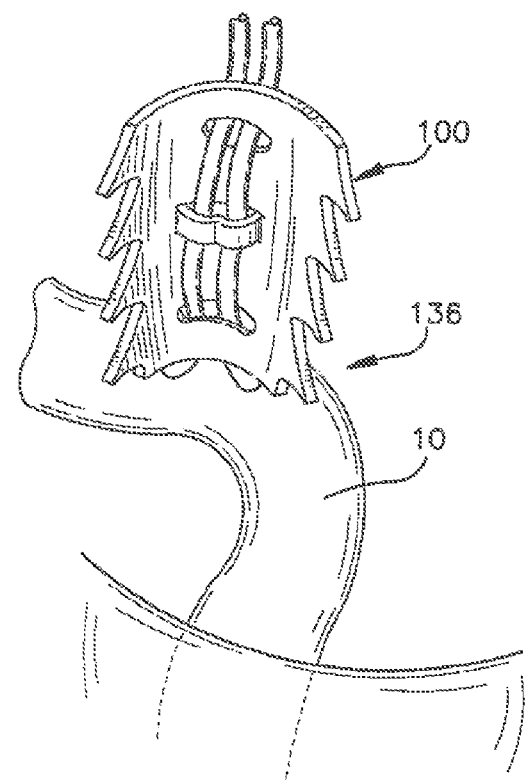

FIGS. 21A-D illustrate a "tether" approach according to the present invention, wherein a suture loop 136 is disposed through the biceps tendon 10. Like the other approach, the implant 100 is configured to be pulled down and engage biological soft tissue as shown in FIG. 21B. A "banjo-style" implant 100 can be threaded onto the two free ends of the suture loop 136, as shown in FIG. 21C. The implant 100 is approximated to the tendon 10, as shown in FIG. 21D, after which the tendon 10 is permitted to retract into the bicipital sheath 22, as shown in FIG. 21B. The implant 100 engages bicipital groove 18 and bicipital sheath 22, thus preventing further retraction of the tendon 10.

Figure 22A:
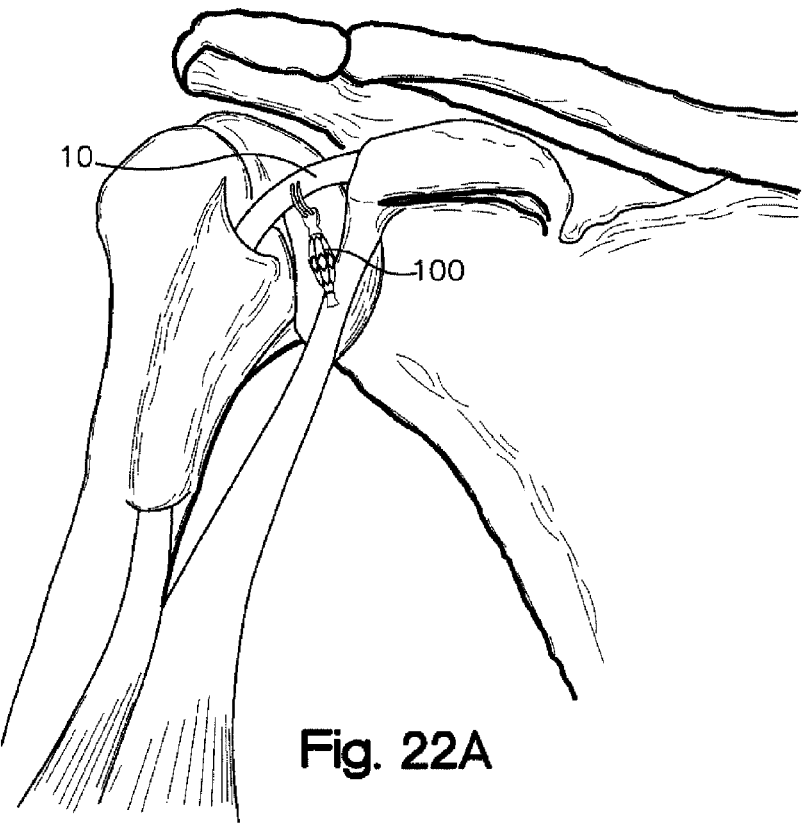
FIGS. 22A-D illustrate another biological soft tissue implant attached to the biceps tendon and the procedure associated therewith in accordance with the present invention.
Figure 22B:
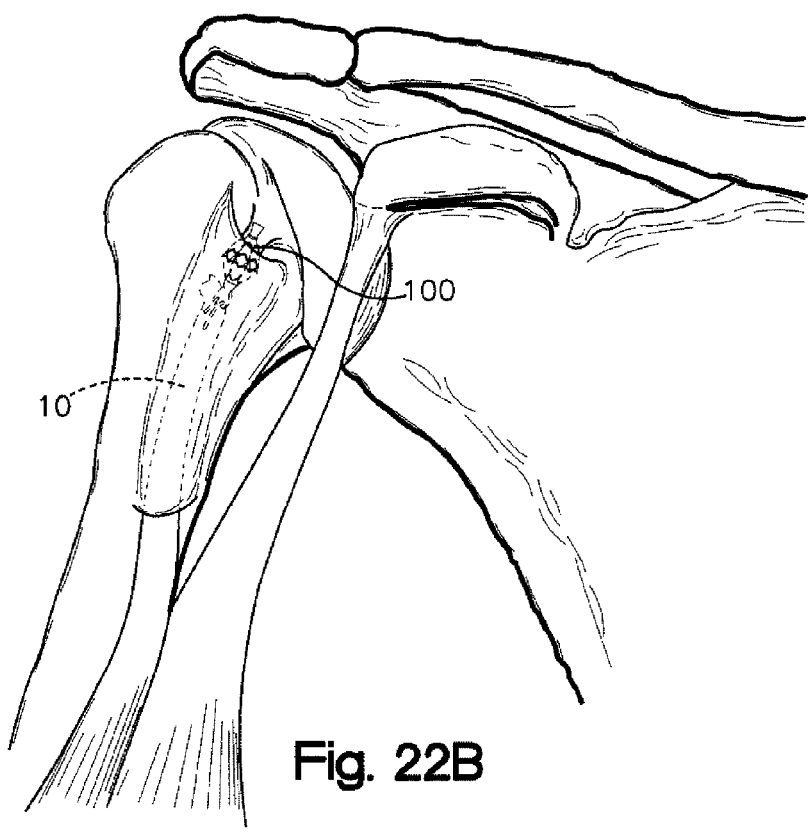
Figure 22C:
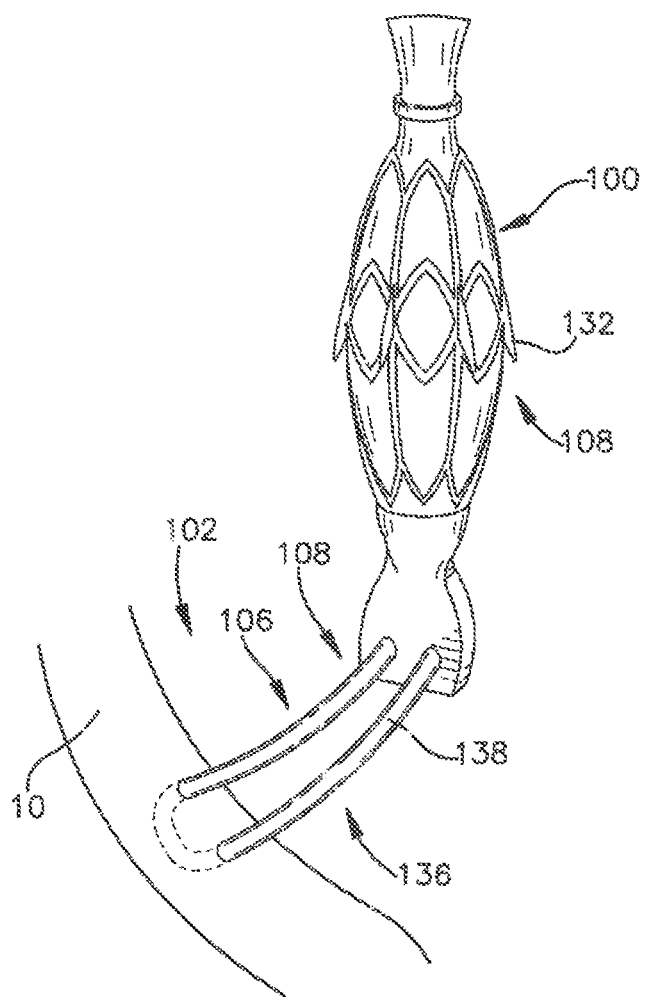
Figure 22D:
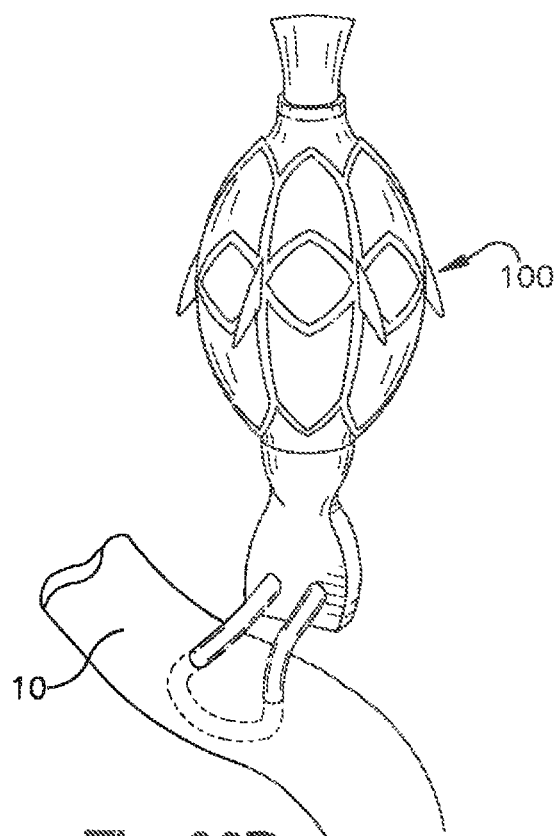

The embodiment illustrated in FIGS. 22A-D is similar in some respects to that shown in FIGS. 21A-D. Provided is an inflatable balloon implant 100, having a structure similar to that of an inflatable stent and functions in accordance with the principles of the invention, in a manner similar to the implant shown in FIGS. 21A-D. More particularly, referring to FIG. 22C, a suture loop 136 is placed in the tendon 10, and the implant 100 is threaded over the free ends of the suture loop 136. Then, as shown in FIG. 22D, the implant 100 is approximated to the tendon 10, and inflated to expanded size. Then, as shown in FIG. 22B, the tendon 10 is separated from the glenoid and permitted to retract downwardly into the sheath 22. As in the previous embodiment, however, the implant 100 becomes engaged in the bicipital groove 18, and fixed in position, thereby maintaining the attached tendon 10 in a fixed position as well. Thus, further retraction of the biceps tendon 10, and the resultant undesirable effects, are avoided. Alternatively, the tendon may be detached from the glenoid before the implant 100 is sutured to the tendon 10, if desired, as long as the tendon 10 is held in its extended position sufficiently long to permit the suturing and inflation steps to be completed, before retraction into the bicipital groove 18 and bicipital sheath 22.

Figure 23A:
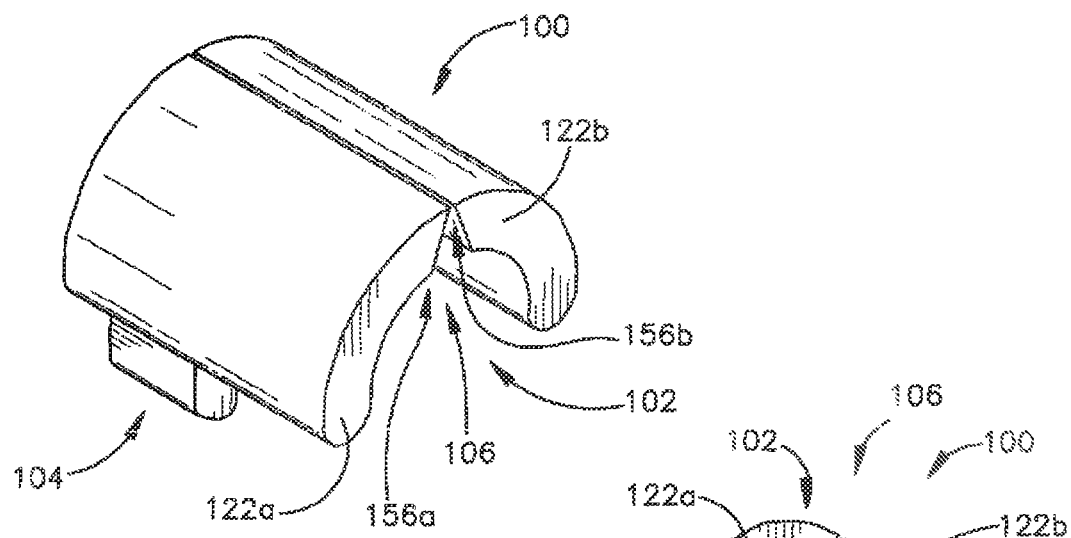
FIGS. 23A-B illustrate top and bottom perspective views of another embodiment of a biological soft tissue implant having multiple cooperating parts that are biasedly engageable.
Figure 23B:
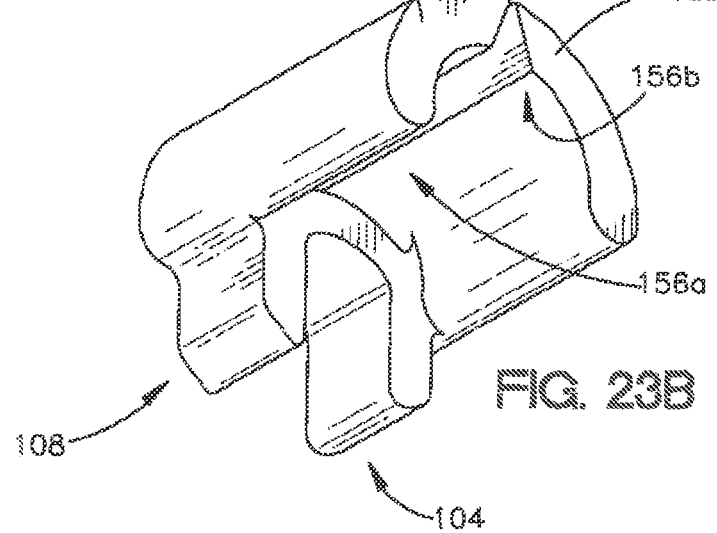
Figure 23C:
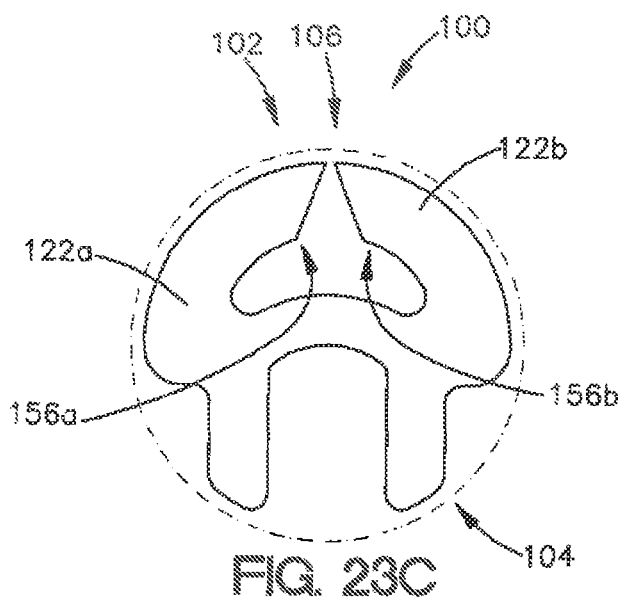
FIG. 23C illustrates top plan view of the implant of FIGS. 23A-B as it might look inside a cannula.

FIGS. 23A-C illustrate an embodiment of a biological soft tissue implant 100 cooperating parts 122a and 122b that are biasedly engageable. FIGS. 23A-B show top and bottom perspective views of the implant 100 and FIG. 23C shows the implant 100 as it may appear within the diameter of a cannula. Illustrated is a biological soft tissue implant 100 having a fastener 102 and anchor 104. The anchor 104 includes tabs 116. The fastener 102 includes cooperating parts 122a and 122b having a gripping surfaces 156a and 156b, respectively, on their interiors. The implant 100 may also include teeth for engaging the implant.

In operation, the implant 100 may be located at the biological soft tissue, such as by being passed through a cannula as shown in FIG. 23C. Once the implant 100 is located at the tissue, the normally closed cooperating parts 122a and 122b are opened by applying pressure to the tabs 116. The biological soft tissue is then located inside the implant 100 and the pressure being applied to the tabs 116 is relieved. The cooperating parts 122a and 122b then clamp onto the biological soft tissue. Once the biological soft tissue is severed, the tabs 116 act as an anchor 104 to prevent the biological soft tissue from retracting beyond a suitable point.

Figure 24A:
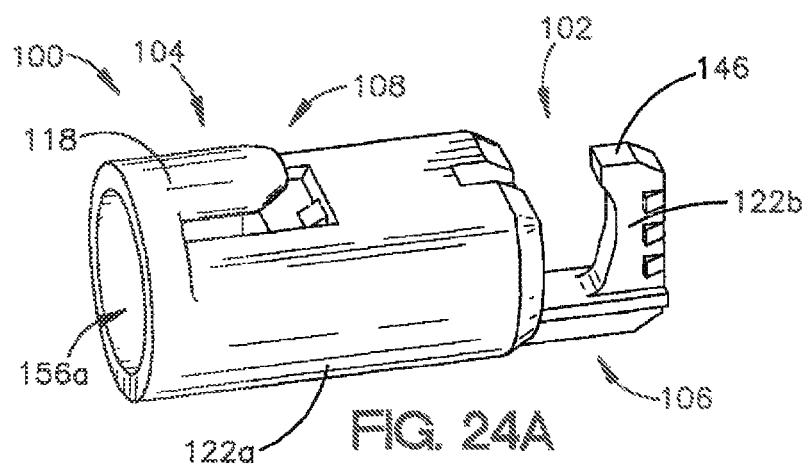
FIGS. 24A-B illustrate perspective views in both open and close positions, respectively, of another embodiment of a slidably engageable implant with a hook and capture mechanism.
Figure 24B:
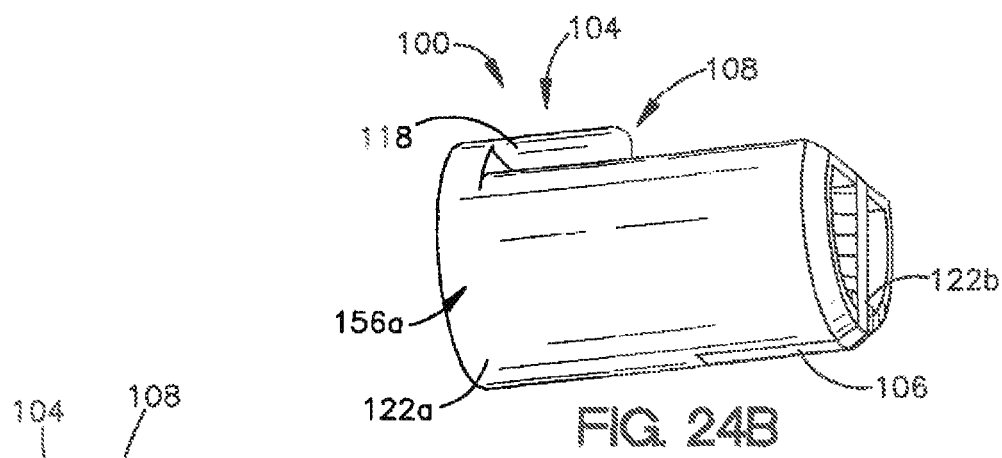
Figure 24C:
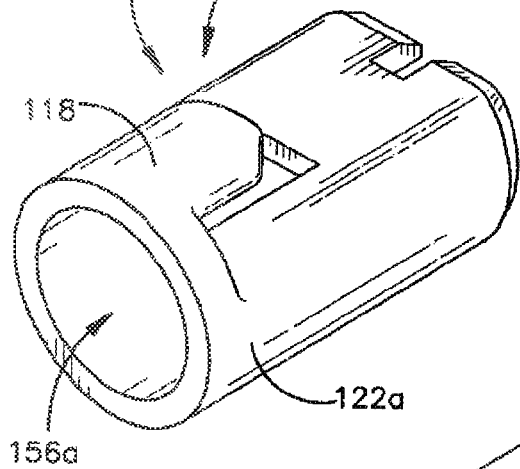
FIGS. 24C-D illustrate perspective views of cooperating parts of the implant of FIGS. 24A-B.
Figure 24D:
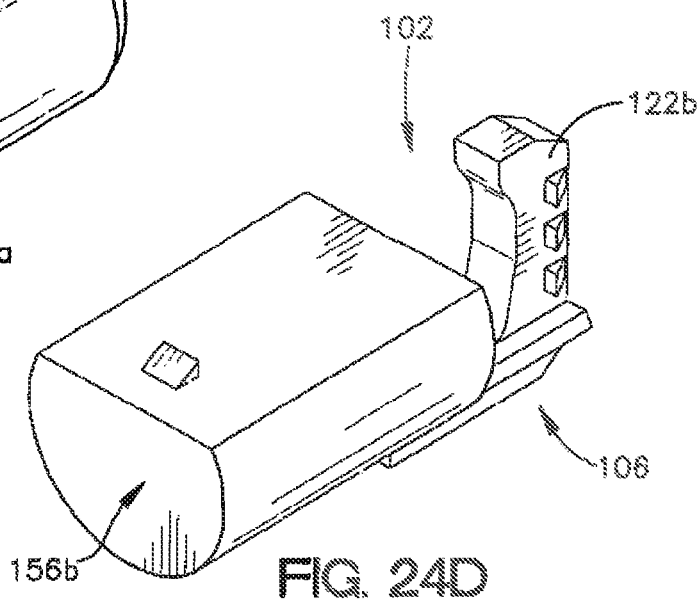

FIGS. 24A-D illustrate another embodiment of a slidably engageable implant 100 with a hook and capture mechanism. FIGS. 24A-B illustrate perspective views of the implant 100 in both open and close positions, respectively. FIGS. 24C-D illustrate perspective views of cooperating parts 122a and 122b, respectively. Illustrated is a biological soft tissue implant 100 having a fastener 102 and anchor 104. The anchor 104 includes a hook 118. The fastener 102 includes cooperating parts 122a and 122b that are slidably engageable. The implant 100 includes a hook and capture mechanism for capturing the biological soft tissue. The fastener 102 can be described as including both an engaging element 106 and a locking element 108. The engaging element 106 includes the cooperating parts 122a and 122b for trapping the biological soft tissue, as well as the hook and capture mechanism. The locking element 108 may employ snap-fitting parts (not shown) to hold the cooperating parts 122a and 122b together.

In operation the fastener 102 engages the biological soft tissue between the cooperating parts 122a and 122b. When the cooperating parts 122a and 122b are brought together with the soft tissue therebetween, the fastener 102 engages the biological soft tissue. Specifically, the hook captures the biological soft tissue and traps it once the cooperating parts 122a and 122b are brought together. Once engaged, the fastener 102 also includes a locking element 108. Once the fastener 102 is engaged and locked, tension on the biological soft tissue can be relieved such that the soft tissue begins to retract. The hook 118 of the anchor 104 is configured to engage a second biological soft tissue or bone in order to create tension on and secure the first or damaged biological soft tissue. With reference to the biceps tendon 10, the hook 118 would engage the transverse ligament (not shown) or sheath 22 after the implant 100 is secured to the tendon 10 in order to prevent a Popeye Sign. This engagement of the hook 118 with the sheath 22 can be similar to the engagement described above with reference to FIGS. 2A and 2B or the hook 118 can engage an interior of the sheath 22 in order to prevent a Popeye Sign.

FIGS. 25A-D illustrate an embodiment of a biological soft tissue implant having a suture wrapped around the implant 100 and biological soft tissue. FIG. 25A illustrates a perspective view of the implant 100 without the suture. FIGS. 25B-D illustrate top, side and bottom elevation views, respectively, of the implant 100 and suture in combination 150. Illustrated is a biological soft tissue implant 100 having a fastener 102 and anchor 104. The anchor 104 includes a hook 118. The fastener 102 includes a retaining ring 110 in combination with a suture 150, as well as knots 148 or beads or ratchet mechanism (not shown) such as that found on a common cable tie. The fastener 102 can be described as including both an engaging element 106 and a locking element 108. The engaging element 106 includes retaining ring 110 having a gripping surface 156 with slots 130 in combination with a suture 150. The locking element 108 may include knots 148, beads or ratchet mechanism (not shown).

In operation the suture 150 is preferably wrapped around the ring 110 during manufacture and a hook-shaped probe is used to pull the biological soft tissue into the retaining ring 110. The biological soft tissue may be doubled within the ring 110. Tension is then applied to the suture 150 to cinch the biological soft tissue against the inner wall or gripping surface 156 of the ring 110. The suture may then be locked in place using a locking element such as those described above. The hook 118 of the anchor 104 is configured to engage a second biological soft tissue or bone in order to create tension on and secure the first or damaged biological soft tissue.

Figure 26A:
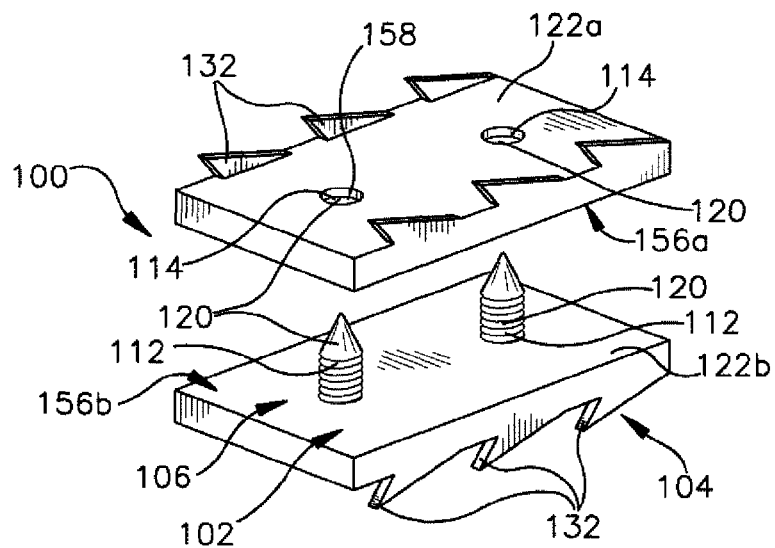
FIGS. 26A-B illustrate open and closed perspective views of another embodiment of a biological soft tissue implant having cooperating parts that are snapably engageable.
Figure 26B:
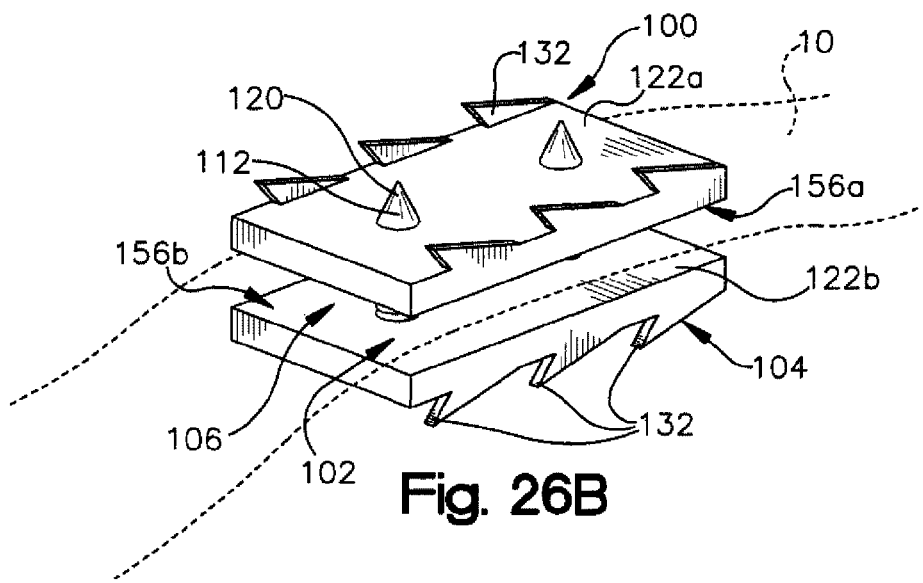

FIGS. 26A-B illustrate perspective views of open and closed configurations of an embodiment of a biological soft tissue implant 100 having cooperating parts 122a and 122b that are snapably engageable. Illustrated is a biological soft tissue implant 100 having a fastener 102 and anchor 104. The anchor 104 includes barbs 132. The fastener 102 includes cooperating parts 122a and 122b having a gripping surfaces 156a and 156b, respectively. The gripping surface 156a includes holes 114. The fastener 102 can be described as including both an engaging element 106 and a locking element 108. The engaging element 106 includes the cooperating parts 122a and 122b for trapping the biological soft tissue, the spikes 112 and the gripping surface 156a and 156b with holes 114. The locking element 108 includes snap-fitting parts 120.

Figure 27:
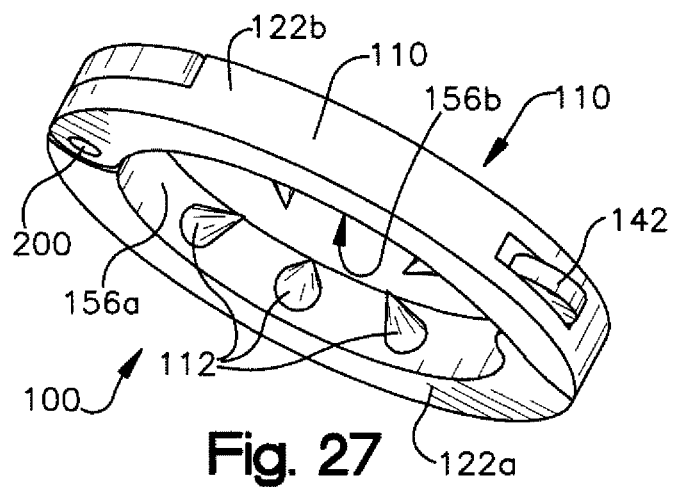
FIG. 27 illustrates a perspective view of another embodiment of a biological soft tissue implant having cooperating parts that form a retaining ring.

FIG. 27 illustrates an embodiment of a biological soft tissue implant 100 having a retaining ring 110. The implant 100 includes cooperating parts 122a and 122b that are hookably or snapably engageable. The cooperating parts 122a and 122b have a gripping surfaces 156a and 156b, respectively. The implant further includes spikes 112 on the gripping surface 156, and a hinge 200 connecting the cooperating parts 122a and 122b on one end, with a latch locking or snapping the cooperating parts 122a and 122b together. When connected, the cooperating parts 122a and 122b form a retaining ring 110. The engaging element 106 includes the cooperating parts 122a and 122b for trapping the biological soft tissue, the spikes 112 and the gripping surfaces 156a and 156b. The locking element 108 includes snap-fitting parts 120.

Figure 28:
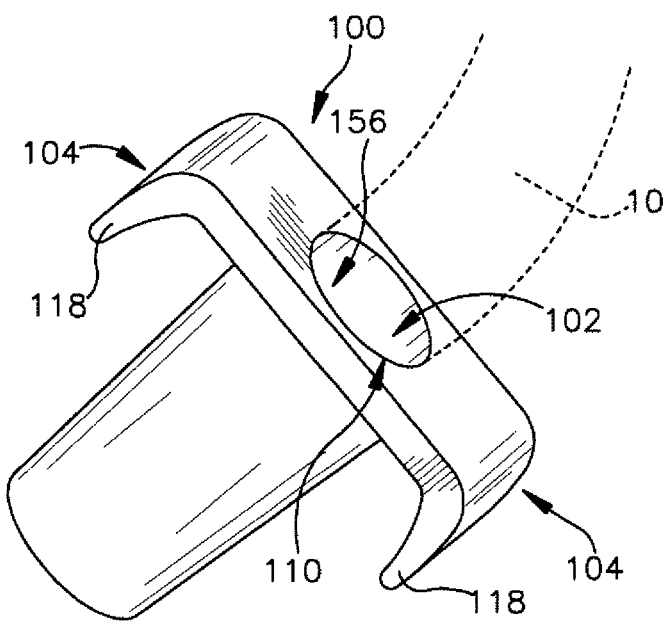
FIG. 28 illustrates a perspective view of another embodiment of a biological soft tissue implant having a retaining ring and two laterally extending beams with hooks.
Figures 31A, 31B:
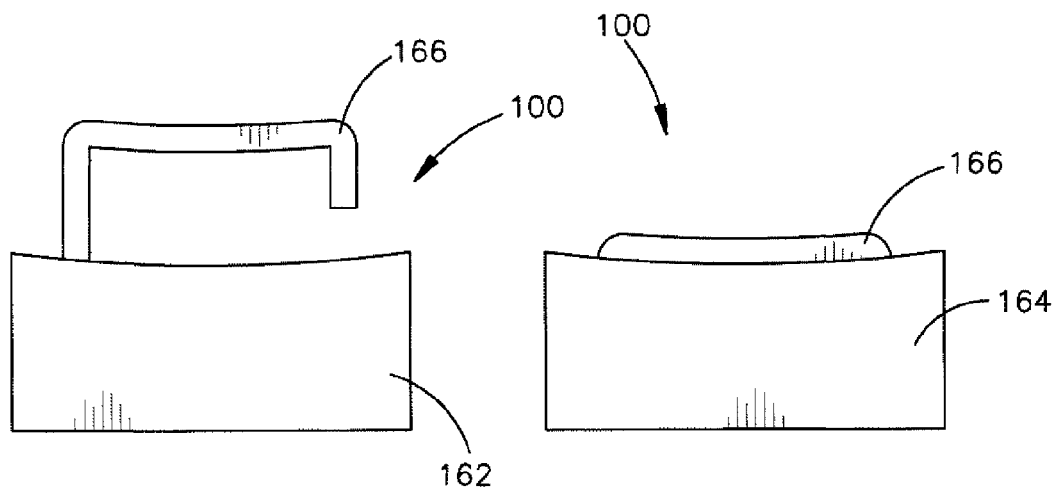
FIGS. 31A-E illustrate perspective and front elevation views of another embodiment of a biological soft tissue implant having multiple biasedly engageable parts and including a hook and capture mechanism.
Figures 31C, 31D:
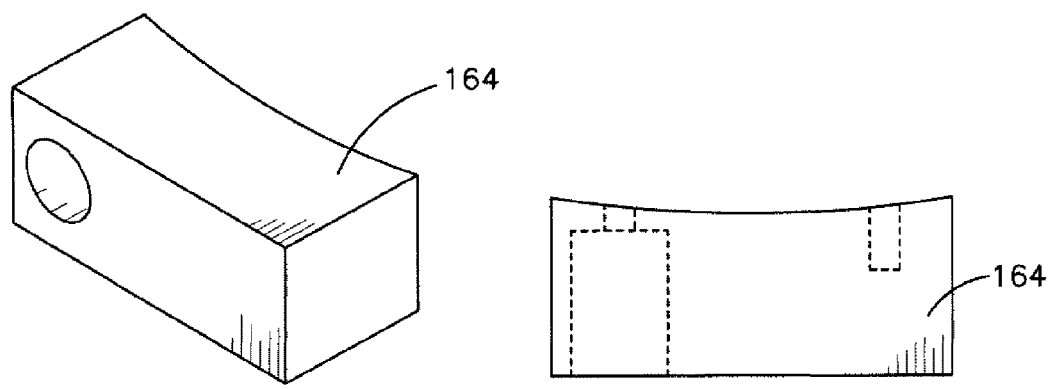
Figure 31E:
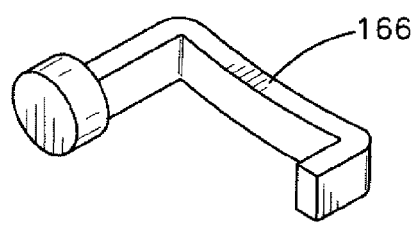

FIG. 28 shows another alternative embodiment of the implant 100 comprising an implant 100 with a retaining ring 110 and two laterally extending beams with hooks 118. The implant has a fastener 102 and anchor 104. The anchor 104 includes beams with hooks 118. The fastener 102 includes a retaining ring 110 with a gripping surface 156 where the retaining ring can be crimped around the biological soft tissue. The fastener 102 can be described as including both an engaging element 106 and a locking element 108. The engaging element 106 includes the retaining ring 110 and gripping surface 156 while the locking element may include crimping.

FIGS. 29-30 show alternative embodiments of the implant 100 comprising cooperating parts 122a and 122b that are biasedly engageable. The implant 100 has a fastener 102 and anchor 104. The anchor 104 includes tabs 116. The fastener includes biasedly engageable cooperating parts 122a and 122b having gripping surfaces 156a and 156b, respectively, and teeth 152.

In operation, the implant 100 may be placed on the biological soft tissue after being passed through a cannula, which are commonly used during arthroscopic procedures. Once the implant 100 is located at the tissue, the normally closed cooperating parts 122a and 122b are opened by applying pressure to the tabs 116. The biological soft tissue is then located inside the implant 100 and the pressure being applied to the tabs 116 is removed. The cooperating parts 122a and 122b, with gripping surfaces 156a and 156b and teeth 152 then clamp onto the biological soft tissue. Once the biological soft tissue is severed, the tabs 116 act as an anchor 104 to prevent the biological soft tissue from retracting beyond a suitable point.

FIGS. 31A-E show an alternative embodiment of the implant 100 comprising cooperating parts 122a and 122b that are biasedly engageable. The implant 100 further includes a hook and capture mechanism. The implant 100 has a fastener 102 that includes a body 164 and normally closed retaining clip 166. The retaining clip 166 traps the biological soft tissue between the body 164 and retaining clip 166.

It should be noted that, while the devices disclosed in the present application have been discussed in connection with biceps tendon treatment procedures, they could be extended to other applications, other types of tendon treatment, soft tissue to soft tissue treatment, fixation of soft tissue to another soft tissue, and tendon fixation, for example. Thus, all of the terms used herein are descriptive rather than limiting, and many changes, modifications, and substitutions may be made by one having ordinary skill in the art without departing from the spirit and scope of the invention. Moreover, while the present invention has been described in association with several exemplary embodiments, the described embodiments are to be considered in all respects as illustrative and not restrictive. Such other features, aspects, variations, modifications, and substitution of equivalents may be made without departing from the spirit and scope of this invention which is intended to be limited solely by the scope of the following claims. Also, it will be appreciated that features and parts illustrated in one embodiment may be used, or may be applicable, in the same or in a similar way in other embodiments.

Having described the invention, the following is claimed:

1. A method for biceps tenodesis comprising the steps of: attaching an implant to the long head of a biceps tendon; severing the long head of the biceps tendon; and releasing the biceps tendon after the implant is attached to the long head to permit the biceps tendon to retract, the retraction of the biceps tendon moving the implant into engagement with a bicipital tunnel bounded by a bicipital sheath, a transverse ligament, and a bicipital groove to anchor the severed tendon and prevent the severed tendon from retracting down through the bicipital tunnel.

2. The method of claim 1 further comprising the step of delivering the implant to the biceps tendon arthroscopically.

3. The method of claim 1 wherein the step of attaching the implant is performed before the step of severing the long head.

4. The method of claim 1 wherein the step of severing the long head is performed before the step of attaching the implant.

5. The method of claim 4 further comprising the steps of: holding the biceps tendon in place prior to severing the long head.

6. The method of claim 1 wherein the engagement of the implant with the bicipital tunnel includes at least one of: engaging the implant with the top of the bicipital tunnel and engaging the implant with the inside of the bicipital tunnel.

7. The method of claim 1 wherein the engagement of the implant with the bicipital tunnel comprises resting at least a portion of the implant against the top of the bicipital tunnel.

8. The method of claim 1 wherein the engagement of the implant with the bicipital tunnel includes at least one of: engaging the implant with soft tissue and engaging the implant with bony tissue.

9. The method of claim 8 wherein engaging the implant with soft tissue includes at least one of: the implant pushing into soft tissue in response to the retraction of the biceps tendon, the implant digging into soft tissue in response to the retraction of the biceps tendon, and the implant penetrating into soft tissue in response to the retraction of the biceps tendon.

10. The method of claim 8 wherein engaging the implant with bony tissue does not include penetrating into bone.

11. The method of claim 1 including engaging two cooperating parts of a fastener of the implant with the biceps tendon to connect the implant to the biceps tendon, locking the two cooperating parts to prevent the separation of the two cooperating parts following engagement of the biceps tendon, and engaging the bicipital tunnel with an anchor of the implant protruding from the fastener.

12. The method of claim 11 including providing the fastener with at least one of: at least one spike, ridges, grooves, at least one latch, at least one suture, at least one hinge, at least one crimping deformation, engageable cooperating parts, at least one gripping surface, at least one retaining ring, at least one gripping beam, or at least one hook and capture mechanism.

13. The method of claim 11 including snapably engaging, slidably engaging, hookably engaging, rotatably engaging, or biasedly engaging the cooperating parts to each other.

14. The method of claim 11 including providing the anchor with at least one of: at least one barb, at least one spike, at least one flap, at least one tab, at least one bar, at least one beam, at least one hook, a pointed implant end configured to anchor when the implant device toggles, or at least one expansion mechanism.

15. The method of claim 11 including locking the cooperating parts to each other with at least one of: snap-fitting parts, crimping, biasing, at least one knot, press-fitting, at least one thread, at least one barb, at least one pin, at least one receiver, at least one retaining surface, riveting, swaging, cold shaping, welding.

16. The method of claim 11 including providing the cooperating parts with at least one gripping surface engaging the biceps tendon having at least one of: at least one barb, at least one spike, at least one hole, at least one slot, ridges, grooves, serrations, teeth, or surface texture.

17. The method of claim 11 including piercing the biceps tendon with at least one spike between the two cooperating parts of the fastener to connect the two cooperating parts to the biceps tendon and providing the anchor with a hook extending from one of the two cooperating parts.

18. The method of claim 17 including extending the at least one spike on one of the cooperating parts-through the biceps tendon and into an opening in the other cooperating part.

19. The method of claim 18 including extending the at least one spike of one of the cooperating parts through the biceps tendon and snapping the spike into an opening of the other cooperating part.

20. The method of claim 19 including extending the spike from a biceps tendon gripping surface of the one cooperating part and extending the opening through a biceps tendon gripping surface of the other cooperating part.

21. The method of claim 8 wherein engaging the implant with soft tissue does not include penetrating through the soft tissue.

* * * * *